United States Patent
Metzger et al.

(10) Patent No.: US 8,764,760 B2
(45) Date of Patent: Jul. 1, 2014

(54) PATIENT-SPECIFIC BONE-CUTTING GUIDANCE INSTRUMENTS AND METHODS

(75) Inventors: Robert Metzger, Wakarusa, IN (US); Troy W. Hershberger, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 249 days.

(21) Appl. No.: 13/175,142

(22) Filed: Jul. 1, 2011

(65) Prior Publication Data

US 2013/0006250 A1 Jan. 3, 2013

(51) Int. Cl.
*A61B 17/58* (2006.01)

(52) U.S. Cl.
USPC .......................................... 606/88

(58) Field of Classification Search
USPC ............... 606/79–80, 86 R, 87–89, 96–98
See application file for complete search history.

(56) References Cited

U.S. PATENT DOCUMENTS

| | | |
|---|---|---|
| 1,480,285 A | 1/1924 | Moore |
| 2,181,746 A | 11/1939 | Siebrandt |
| 2,407,845 A | 9/1946 | Nemeyer |
| 2,618,913 A | 11/1952 | Plancon et al. |
| 2,910,978 A | 11/1959 | Urist |
| 3,840,904 A | 10/1974 | Tronzo |
| 4,246,895 A | 1/1981 | Rehder |
| 4,306,866 A | 12/1981 | Weissman |
| 4,324,006 A | 4/1982 | Charnley |
| 4,421,112 A | 12/1983 | Mains et al. |
| 4,436,684 A | 3/1984 | White |
| 4,457,306 A | 7/1984 | Borzone |
| 4,475,549 A | 10/1984 | Oh |
| 4,506,393 A | 3/1985 | Murphy |
| 4,524,766 A | 6/1985 | Petersen |
| 4,529,080 A | 7/1985 | Dolan |
| 4,531,623 A | 7/1985 | Arai et al. |
| 4,619,658 A | 10/1986 | Pappas et al. |
| 4,621,630 A | 11/1986 | Kenna |
| 4,632,111 A | 12/1986 | Roche |
| 4,633,862 A | 1/1987 | Petersen |
| 4,663,720 A | 5/1987 | Duret et al. |

(Continued)

FOREIGN PATENT DOCUMENTS

| | | |
|---|---|---|
| CA | 2447694 A1 | 12/2002 |
| CA | 2501041 A1 | 4/2004 |

(Continued)

OTHER PUBLICATIONS

"Amazing Precision. Beautiful Results. The next evolution of MAKOplasty® is here," brochure. (Feb. 2009) MAKO Surgical Corp. 6 pages.

(Continued)

*Primary Examiner* — Matthew Lawson
(74) *Attorney, Agent, or Firm* — Harness, Dickey

(57) ABSTRACT

An orthopedic device for cutting or resurfacing an outer bone surface of a bone of a patient includes first and second guides. Each guide has a patient-specific surface preoperatively configured as a negative surface of a portion of the outer bone surface of the bone and a plurality of elongated slots. The elongated slots of the second guide are offset relative to the elongated slots of the first guide and configured for guiding a tool to resurface the outer bone surface.

17 Claims, 8 Drawing Sheets

(56) References Cited

U.S. PATENT DOCUMENTS

| | | |
|---|---|---|
| 4,689,984 A | 9/1987 | Kellner |
| 4,695,283 A | 9/1987 | Aldinger |
| 4,696,292 A | 9/1987 | Heiple |
| 4,703,751 A | 11/1987 | Pohl |
| 4,704,686 A | 11/1987 | Aldinger |
| 4,706,660 A | 11/1987 | Petersen |
| 4,719,907 A | 1/1988 | Banko et al. |
| 4,721,104 A | 1/1988 | Kaufman et al. |
| 4,722,330 A | 2/1988 | Russell et al. |
| 4,759,350 A | 7/1988 | Dunn et al. |
| 4,778,474 A | 10/1988 | Homsy |
| 4,800,874 A | 1/1989 | David et al. |
| 4,821,213 A | 4/1989 | Cline et al. |
| 4,822,365 A | 4/1989 | Walker et al. |
| 4,841,975 A | 6/1989 | Woolson |
| 4,846,161 A | 7/1989 | Roger |
| 4,871,975 A | 10/1989 | Nawata et al. |
| 4,893,619 A | 1/1990 | Dale et al. |
| 4,896,663 A | 1/1990 | Vandewalls |
| 4,907,577 A | 3/1990 | Wu |
| 4,927,422 A | 5/1990 | Engelhardt |
| 4,936,862 A | 6/1990 | Walker et al. |
| 4,952,213 A | 8/1990 | Bowman et al. |
| 4,959,066 A | 9/1990 | Dunn et al. |
| 4,976,737 A | 12/1990 | Leake |
| 4,979,949 A | 12/1990 | Matsen, III et al. |
| 4,985,037 A | 1/1991 | Petersen |
| 5,002,579 A | 3/1991 | Copf et al. |
| 5,007,936 A | 4/1991 | Woolson |
| 5,027,672 A | 7/1991 | Salvatori et al. |
| 5,030,221 A | 7/1991 | Buechel et al. |
| 5,041,117 A | 8/1991 | Engelhardt |
| 5,053,037 A | 10/1991 | Lackey |
| 5,053,039 A | 10/1991 | Hofmann et al. |
| 5,056,351 A | 10/1991 | Stiver et al. |
| 5,086,401 A | 2/1992 | Glassman et al. |
| 5,098,383 A | 3/1992 | Hemmy et al. |
| 5,098,436 A | 3/1992 | Ferrante et al. |
| 5,108,425 A | 4/1992 | Hwang |
| 5,122,144 A | 6/1992 | Bert et al. |
| 5,129,908 A | 7/1992 | Petersen |
| 5,129,909 A | 7/1992 | Sutherland |
| 5,133,760 A | 7/1992 | Petersen et al. |
| 5,140,777 A | 8/1992 | Ushiyama et al. |
| 5,150,304 A | 9/1992 | Berchem et al. |
| 5,176,684 A | 1/1993 | Ferrante et al. |
| 5,194,066 A | 3/1993 | Van Zile |
| 5,234,433 A | 8/1993 | Bert et al. |
| 5,246,444 A | 9/1993 | Schreiber |
| 5,253,506 A | 10/1993 | Davis et al. |
| 5,258,032 A | 11/1993 | Bertin |
| 5,261,915 A | 11/1993 | Durlacher et al. |
| 5,274,565 A | 12/1993 | Reuben |
| 5,299,288 A | 3/1994 | Glassman et al. |
| 5,300,077 A | 4/1994 | Howell |
| 5,320,529 A | 6/1994 | Pompa |
| 5,320,625 A | 6/1994 | Bertin |
| 5,323,697 A | 6/1994 | Schrock |
| 5,342,366 A | 8/1994 | Whiteside et al. |
| 5,344,423 A | 9/1994 | Dietz et al. |
| 5,360,446 A | 11/1994 | Kennedy |
| 5,364,402 A | 11/1994 | Mumme et al. |
| 5,368,858 A | 11/1994 | Hunziker |
| 5,370,692 A | 12/1994 | Fink et al. |
| 5,370,699 A | 12/1994 | Hood et al. |
| 5,405,395 A | 4/1995 | Coates |
| 5,408,409 A | 4/1995 | Glassman et al. |
| 5,411,521 A | 5/1995 | Putnam et al. |
| 5,415,662 A | 5/1995 | Ferrante et al. |
| 5,417,694 A | 5/1995 | Marik et al. |
| 5,438,263 A | 8/1995 | Dworkin et al. |
| 5,440,496 A | 8/1995 | Andersson et al. |
| 5,448,489 A | 9/1995 | Reuben |
| 5,449,360 A | 9/1995 | Schreiber |
| 5,452,407 A | 9/1995 | Crook |
| 5,454,816 A | 10/1995 | Ashby |
| 5,462,550 A | 10/1995 | Dietz et al. |
| 5,463,911 A | 11/1995 | Knoedel et al. |
| 5,472,415 A | 12/1995 | King et al. |
| 5,474,559 A | 12/1995 | Bertin et al. |
| 5,490,854 A | 2/1996 | Fisher et al. |
| 5,496,324 A | 3/1996 | Barnes |
| 5,507,833 A | 4/1996 | Bohn |
| 5,514,519 A | 5/1996 | Neckers |
| 5,520,695 A | 5/1996 | Luckman |
| 5,527,317 A | 6/1996 | Ashby et al. |
| 5,539,649 A | 7/1996 | Walsh et al. |
| 5,540,695 A | 7/1996 | Levy |
| 5,545,222 A | 8/1996 | Bonutti |
| 5,549,688 A | 8/1996 | Ries et al. |
| 5,554,190 A | 9/1996 | Draenert |
| 5,560,096 A | 10/1996 | Stephens |
| 5,571,110 A | 11/1996 | Matsen, III et al. |
| 5,578,037 A | 11/1996 | Sanders et al. |
| 5,595,703 A | 1/1997 | Swaelens et al. |
| 5,607,431 A | 3/1997 | Dudasik et al. |
| 5,613,969 A | 3/1997 | Jenkins, Jr. |
| 5,620,448 A | 4/1997 | Puddu |
| 5,634,927 A | 6/1997 | Houston et al. |
| 5,641,323 A | 6/1997 | Caldarise |
| 5,658,294 A | 8/1997 | Sederholm |
| 5,662,656 A | 9/1997 | White |
| 5,662,710 A | 9/1997 | Bonutti |
| 5,671,018 A | 9/1997 | Ohara et al. |
| 5,676,668 A | 10/1997 | McCue et al. |
| 5,677,107 A | 10/1997 | Neckers |
| 5,681,354 A | 10/1997 | Eckhoff |
| 5,682,886 A | 11/1997 | Delp et al. |
| 5,683,469 A | 11/1997 | Johnson et al. |
| 5,690,635 A | 11/1997 | Matsen, III et al. |
| 5,702,460 A | 12/1997 | Carls et al. |
| 5,702,464 A | 12/1997 | Lackey et al. |
| 5,704,941 A | 1/1998 | Jacober et al. |
| 5,709,689 A | 1/1998 | Ferrante et al. |
| 5,720,752 A | 2/1998 | Elliott et al. |
| 5,722,978 A | 3/1998 | Jenkins, Jr. |
| 5,725,376 A | 3/1998 | Poirier |
| 5,725,593 A | 3/1998 | Caracciolo |
| 5,735,277 A | 4/1998 | Schuster |
| 5,748,767 A | 5/1998 | Raab |
| 5,749,875 A | 5/1998 | Puddu |
| 5,749,876 A | 5/1998 | Duvillier et al. |
| 5,762,125 A | 6/1998 | Mastrorio |
| 5,768,134 A | 6/1998 | Swaelens et al. |
| 5,769,092 A | 6/1998 | Williamson, Jr. |
| 5,776,200 A | 7/1998 | Johnson et al. |
| 5,786,217 A | 7/1998 | Tubo et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,826,462 A | 10/1998 | Schaefer |
| 5,835,619 A | 11/1998 | Morimoto et al. |
| 5,860,981 A | 1/1999 | Bertin et al. |
| 5,871,018 A | 2/1999 | Delp et al. |
| 5,876,456 A | 3/1999 | Sederholm et al. |
| 5,879,398 A | 3/1999 | Swarts et al. |
| 5,879,402 A | 3/1999 | Lawes et al. |
| 5,880,976 A | 3/1999 | DiGioia, III et al. |
| 5,885,297 A | 3/1999 | Matsen, III |
| 5,885,298 A | 3/1999 | Herrington et al. |
| 5,888,219 A | 3/1999 | Bonutti |
| 5,895,389 A | 4/1999 | Schenk et al. |
| 5,899,907 A | 5/1999 | Johnson |
| 5,901,060 A | 5/1999 | Schall et al. |
| 5,911,724 A | 6/1999 | Wehrli |
| 5,921,988 A | 7/1999 | Legrand |
| 5,925,049 A | 7/1999 | Gustilo et al. |
| 5,942,370 A | 8/1999 | Neckers |
| 5,967,777 A | 10/1999 | Klein et al. |
| 5,976,149 A | 11/1999 | Masini |
| 5,980,526 A | 11/1999 | Johnson et al. |
| 6,033,415 A | 3/2000 | Mittelstadt et al. |
| 6,059,789 A | 5/2000 | Dinger et al. |
| 6,059,833 A | 5/2000 | Doets |

(56) References Cited

U.S. PATENT DOCUMENTS

| | | |
|---|---|---|
| 6,086,593 A | 7/2000 | Bonutti |
| 6,120,510 A | 9/2000 | Albrektsson et al. |
| 6,120,544 A | 9/2000 | Grundei et al. |
| 6,126,690 A | 10/2000 | Ateshian et al. |
| 6,126,692 A | 10/2000 | Robie et al. |
| 6,136,033 A | 10/2000 | Suemer |
| 6,156,069 A | 12/2000 | Amstutz |
| 6,159,217 A | 12/2000 | Robie et al. |
| 6,161,080 A | 12/2000 | Aouni-Ateshian et al. |
| 6,164,151 A | 12/2000 | Dutson et al. |
| 6,187,010 B1 | 2/2001 | Masini |
| 6,195,615 B1 | 2/2001 | Lysen |
| 6,203,546 B1 | 3/2001 | MacMahon |
| 6,205,411 B1 | 3/2001 | DiGioia, III et al. |
| 6,206,927 B1 | 3/2001 | Fell et al. |
| 6,210,445 B1 | 4/2001 | Zawadzki |
| 6,238,435 B1 | 5/2001 | Meulink et al. |
| 6,254,604 B1 | 7/2001 | Howell |
| 6,258,097 B1 | 7/2001 | Cook et al. |
| 6,264,698 B1 | 7/2001 | Lawes et al. |
| 6,270,529 B1 | 8/2001 | Terrill-Grisoni et al. |
| 6,273,891 B1 | 8/2001 | Masini |
| 6,290,727 B1 | 9/2001 | Otto et al. |
| 6,293,971 B1 | 9/2001 | Nelson et al. |
| 6,310,269 B1 | 10/2001 | Friese et al. |
| 6,312,258 B1 | 11/2001 | Ashman |
| 6,312,473 B1 | 11/2001 | Oshida |
| 6,319,285 B1 | 11/2001 | Chamier et al. |
| 6,325,829 B1 | 12/2001 | Schmotzer |
| 6,343,987 B2 | 2/2002 | Hayama et al. |
| 6,354,011 B1 | 3/2002 | Albrecht |
| 6,361,563 B2 | 3/2002 | Terrill-Grisoni et al. |
| 6,379,299 B1 | 4/2002 | Borodulin et al. |
| 6,379,388 B1 | 4/2002 | Ensign et al. |
| 6,383,228 B1 | 5/2002 | Schmotzer |
| 6,391,251 B1 | 5/2002 | Keicher et al. |
| 6,395,005 B1 | 5/2002 | Lovell |
| 6,427,698 B1 | 8/2002 | Yoon |
| 6,459,948 B1 | 10/2002 | Ateshian et al. |
| 6,463,351 B1 | 10/2002 | Clynch |
| 6,475,243 B1 | 11/2002 | Sheldon et al. |
| 6,482,236 B2 | 11/2002 | Habecker |
| 6,488,715 B1 | 12/2002 | Pope et al. |
| 6,503,255 B1 | 1/2003 | Albrektsson et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,519,998 B2 | 2/2003 | Ertl et al. |
| 6,520,964 B2 | 2/2003 | Tallarida et al. |
| 6,533,737 B1 | 3/2003 | Brosseau et al. |
| 6,547,823 B2 | 4/2003 | Scarborough et al. |
| 6,554,837 B1 | 4/2003 | Hauri et al. |
| 6,556,008 B2 | 4/2003 | Thesen |
| 6,558,391 B2 | 5/2003 | Axelson, Jr. et al. |
| 6,558,428 B2 | 5/2003 | Park |
| 6,564,085 B2 | 5/2003 | Meaney et al. |
| 6,567,681 B1 | 5/2003 | Lindequist |
| 6,575,980 B1 | 6/2003 | Robie et al. |
| 6,575,982 B1 | 6/2003 | Bonutti |
| 6,591,581 B2 | 7/2003 | Schmieding |
| 6,605,293 B1 | 8/2003 | Giordano et al. |
| 6,619,153 B2 | 9/2003 | Smith et al. |
| 6,622,567 B1 | 9/2003 | Hamel et al. |
| 6,629,999 B1 | 10/2003 | Serafin, Jr. |
| 6,641,617 B1 | 11/2003 | Merrill et al. |
| 6,682,566 B2 | 1/2004 | Draenert |
| 6,696,073 B2 | 2/2004 | Boyce et al. |
| 6,697,664 B2 | 2/2004 | Kienzl, III et al. |
| 6,701,174 B1 | 3/2004 | Krause et al. |
| 6,709,462 B2 | 3/2004 | Hanssen |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,749,638 B1 | 6/2004 | Saladino |
| 6,750,653 B1 | 6/2004 | Zou et al. |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,823,871 B2 | 11/2004 | Schmieding |
| 6,827,723 B2 | 12/2004 | Carson |
| 6,887,247 B1 | 5/2005 | Couture et al. |
| 6,905,514 B2 | 6/2005 | Carignan et al. |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,960,216 B2 | 11/2005 | Kolb et al. |
| 6,975,755 B1 | 12/2005 | Baumberg |
| 6,990,220 B2 | 1/2006 | Ellis et al. |
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | McKinnon |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,121,832 B2 | 10/2006 | Hsieh et al. |
| 7,141,053 B2 | 11/2006 | Rosa et al. |
| D533,664 S | 12/2006 | Buttler et al. |
| 7,169,185 B2 | 1/2007 | Sidebotham |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | DiSilvestro et al. |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,275,218 B2 | 9/2007 | Petrella et al. |
| 7,282,054 B2 | 10/2007 | Steffensmeier et al. |
| 7,294,133 B2 | 11/2007 | Zink et al. |
| 7,297,164 B2 | 11/2007 | Johnson et al. |
| 7,309,339 B2 | 12/2007 | Cusick et al. |
| 7,333,013 B2 | 2/2008 | Berger |
| 7,335,231 B2 | 2/2008 | McLean |
| 7,371,260 B2 | 5/2008 | Malinin |
| 7,383,164 B2 | 6/2008 | Aram et al. |
| 7,385,498 B2 | 6/2008 | Dobosz |
| 7,388,972 B2 | 6/2008 | Kitson |
| 7,392,076 B2 | 6/2008 | Moctezuma de La Barrera |
| 7,427,200 B2 | 9/2008 | Noble et al. |
| 7,427,272 B2 | 9/2008 | Richard et al. |
| 7,468,075 B2 | 12/2008 | Lang et al. |
| 7,474,223 B2 | 1/2009 | Nycz et al. |
| 7,488,325 B2 | 2/2009 | Qian |
| 7,494,510 B2 | 2/2009 | Zweymuller |
| 7,517,365 B2 | 4/2009 | Carignan et al. |
| 7,527,631 B2 | 5/2009 | Maroney et al. |
| 7,534,263 B2 | 5/2009 | Burdulis, Jr. et al. |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kelman |
| 7,601,155 B2 | 10/2009 | Petersen |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,646,161 B2 | 1/2010 | Albu-Schaffer et al. |
| 7,651,501 B2 | 1/2010 | Penenberg et al. |

(56) References Cited

U.S. PATENT DOCUMENTS

| | | |
|---|---|---|
| 7,670,345 B2 | 3/2010 | Plassky et al. |
| 7,682,398 B2 | 3/2010 | Croxton et al. |
| 7,695,477 B2 | 4/2010 | Creger et al. |
| 7,695,521 B2 | 4/2010 | Ely et al. |
| 7,699,847 B2 | 4/2010 | Sheldon et al. |
| 7,704,253 B2 | 4/2010 | Bastian et al. |
| 7,723,395 B2 | 5/2010 | Ringeisen et al. |
| D622,854 S | 8/2010 | Otto et al. |
| 7,780,672 B2 | 8/2010 | Metzger et al. |
| 7,780,740 B2 | 8/2010 | Steinberg |
| 7,794,466 B2 | 9/2010 | Merchant et al. |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,879,109 B2 | 2/2011 | Borden et al. |
| 7,892,261 B2 | 2/2011 | Bonutti |
| 7,896,921 B2 | 3/2011 | Smith et al. |
| 7,926,363 B2 | 4/2011 | Miller et al. |
| 7,935,119 B2 | 5/2011 | Ammann et al. |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 7,993,353 B2 | 8/2011 | Rossner et al. |
| 8,062,301 B2 | 11/2011 | Ammann et al. |
| 8,070,752 B2 | 12/2011 | Metzger et al. |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |
| 8,133,230 B2 | 3/2012 | Stevens et al. |
| 8,133,234 B2 | 3/2012 | Meridew et al. |
| 8,137,406 B2 | 3/2012 | Novak et al. |
| 8,160,345 B2 | 4/2012 | Pavlovskaia et al. |
| 8,167,951 B2 | 5/2012 | Ammann et al. |
| 8,170,641 B2 | 5/2012 | Belcher |
| 8,182,489 B2 | 5/2012 | Horacek |
| 8,192,441 B2 | 6/2012 | Collazo |
| 8,192,495 B2 | 6/2012 | Simpson et al. |
| 8,211,112 B2 | 7/2012 | Novak et al. |
| 8,221,430 B2 | 7/2012 | Park et al. |
| 8,241,292 B2 | 8/2012 | Collazo |
| 8,241,293 B2 | 8/2012 | Stone et al. |
| 8,265,790 B2 | 9/2012 | Amiot et al. |
| D669,176 S | 10/2012 | Frey |
| 8,282,646 B2 | 10/2012 | Schoenefeld et al. |
| 8,298,237 B2 | 10/2012 | Schoenefeld et al. |
| 8,303,596 B2 | 11/2012 | Plaßky et al. |
| D672,038 S | 12/2012 | Frey |
| 8,333,772 B2 | 12/2012 | Fox et al. |
| 8,355,773 B2 | 1/2013 | Leitner et al. |
| 8,377,066 B2 | 2/2013 | Katrana et al. |
| 8,398,646 B2 | 3/2013 | Metzger et al. |
| 8,407,067 B2 | 3/2013 | Uthgenannt et al. |
| 8,419,741 B2 | 4/2013 | Carignan et al. |
| 8,430,931 B2 | 4/2013 | Acker et al. |
| 8,439,675 B2 | 5/2013 | De Moyer |
| 8,439,925 B2 | 5/2013 | Marino et al. |
| 8,460,302 B2 | 6/2013 | Park et al. |
| 8,473,305 B2 | 6/2013 | Belcher et al. |
| 8,486,150 B2 | 7/2013 | White et al. |
| 8,532,361 B2 | 9/2013 | Pavlovskaia et al. |
| 8,532,807 B2 | 9/2013 | Metzger |
| 8,535,387 B2 | 9/2013 | Meridew et al. |
| 8,543,234 B2 | 9/2013 | Gao |
| 8,568,487 B2 | 10/2013 | Witt et al. |
| 8,632,547 B2 | 1/2014 | Maxson et al. |
| 2001/0005797 A1 | 6/2001 | Barlow et al. |
| 2001/0011190 A1 | 8/2001 | Park |
| 2001/0021876 A1 | 9/2001 | Terrill-Grisoni et al. |
| 2001/0054478 A1 | 12/2001 | Watanabe et al. |
| 2002/0007294 A1 | 1/2002 | Bradbury et al. |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0107522 A1 | 8/2002 | Picard et al. |
| 2002/0128872 A1 | 9/2002 | Giammattei |
| 2002/0147415 A1 | 10/2002 | Martelli |
| 2002/0193797 A1 | 12/2002 | Johnson et al. |
| 2002/0198528 A1 | 12/2002 | Engh et al. |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson et al. |
| 2003/0039676 A1 | 2/2003 | Boyce et al. |
| 2003/0055502 A1 | 3/2003 | Lang et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |
| 2003/0139817 A1 | 7/2003 | Tuke et al. |
| 2003/0158606 A1 | 8/2003 | Coon et al. |
| 2003/0171757 A1 | 9/2003 | Coon et al. |
| 2003/0216669 A1 | 11/2003 | Lang et al. |
| 2004/0018144 A1 | 1/2004 | Briscoe |
| 2004/0030245 A1 | 2/2004 | Noble et al. |
| 2004/0054372 A1 | 3/2004 | Corden et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0204644 A1 | 10/2004 | Tsougarakis et al. |
| 2004/0204760 A1 | 10/2004 | Fitz et al. |
| 2004/0212586 A1 | 10/2004 | Denny |
| 2004/0220583 A1 | 11/2004 | Pieczynski et al. |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2004/0260301 A1 | 12/2004 | Lionberger et al. |
| 2005/0008887 A1 | 1/2005 | Haymann et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |

(56) References Cited

U.S. PATENT DOCUMENTS

| | | |
|---|---|---|
| 2005/0075641 A1 | 4/2005 | Singhatat et al. |
| 2005/0096535 A1 | 5/2005 | de la Barrera |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0148843 A1 | 7/2005 | Roose |
| 2005/0149042 A1 | 7/2005 | Metzger |
| 2005/0171545 A1 | 8/2005 | Walsh et al. |
| 2005/0177245 A1 | 8/2005 | Leatherbury et al. |
| 2005/0203536 A1 | 9/2005 | Laffargue et al. |
| 2005/0203540 A1 | 9/2005 | Broyles |
| 2005/0216305 A1 | 9/2005 | Funderud |
| 2005/0222571 A1 | 10/2005 | Ryan |
| 2005/0222573 A1 | 10/2005 | Branch et al. |
| 2005/0228393 A1 | 10/2005 | Williams et al. |
| 2005/0234461 A1 | 10/2005 | Burdulis et al. |
| 2005/0234465 A1 | 10/2005 | McCombs et al. |
| 2005/0234468 A1 | 10/2005 | Carson |
| 2005/0240195 A1 | 10/2005 | Axelson et al. |
| 2005/0240267 A1 | 10/2005 | Randall et al. |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro et al. |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady et al. |
| 2006/0100832 A1 | 5/2006 | Bowman |
| 2006/0111722 A1 | 5/2006 | Bouadi |
| 2006/0122616 A1 | 6/2006 | Bennett et al. |
| 2006/0136058 A1 | 6/2006 | Pietrzak |
| 2006/0142657 A1 | 6/2006 | Quaid et al. |
| 2006/0155380 A1 | 7/2006 | Clemow et al. |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0184250 A1 | 8/2006 | Bandoh et al. |
| 2006/0190086 A1 | 8/2006 | Clemow et al. |
| 2006/0195111 A1 | 8/2006 | Couture |
| 2006/0195194 A1 | 8/2006 | Gunther |
| 2006/0195198 A1 | 8/2006 | James |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak et al. |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0293681 A1 | 12/2006 | Claypool et al. |
| 2007/0015995 A1 | 1/2007 | Lang et al. |
| 2007/0016209 A1 | 1/2007 | Ammann et al. |
| 2007/0027680 A1 | 2/2007 | Ashley et al. |
| 2007/0039205 A1 | 2/2007 | Erb et al. |
| 2007/0043582 A1 | 2/2007 | Peveto et al. |
| 2007/0066917 A1 | 3/2007 | Hodorek et al. |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0118055 A1 | 5/2007 | McCombs |
| 2007/0118138 A1 | 5/2007 | Seo et al. |
| 2007/0118243 A1 | 5/2007 | Schroeder et al. |
| 2007/0150068 A1 | 6/2007 | Dong et al. |
| 2007/0156066 A1 | 7/2007 | McGinley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones et al. |
| 2007/0198022 A1 | 8/2007 | Lang et al. |
| 2007/0203430 A1 | 8/2007 | Lang et al. |
| 2007/0203605 A1 | 8/2007 | Melton et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor et al. |
| 2007/0239481 A1 | 10/2007 | DiSilvestro et al. |
| 2007/0244487 A1 | 10/2007 | Ammann et al. |
| 2007/0250169 A1 | 10/2007 | Lang |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0262867 A1 | 11/2007 | Westrick et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0288029 A1 | 12/2007 | Justin et al. |
| 2007/0288030 A1 | 12/2007 | Metzger et al. |
| 2008/0009952 A1 | 1/2008 | Hodge |
| 2008/0015599 A1 | 1/2008 | D'Alessio et al. |
| 2008/0015603 A1 | 1/2008 | Collazo |
| 2008/0015604 A1 | 1/2008 | Collazo |
| 2008/0015605 A1 | 1/2008 | Collazo |
| 2008/0021299 A1 | 1/2008 | Meulink |
| 2008/0021494 A1 | 1/2008 | Schmelzeisen-Redeker et al. |
| 2008/0021567 A1 | 1/2008 | Meulink et al. |
| 2008/0027563 A1 | 1/2008 | Johnson et al. |
| 2008/0033442 A1 | 2/2008 | Amiot et al. |
| 2008/0039850 A1 | 2/2008 | Rowley et al. |
| 2008/0051799 A1 | 2/2008 | Bonutti |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1 | 3/2008 | Wasielewski et al. |
| 2008/0097451 A1 | 4/2008 | Chen et al. |
| 2008/0112996 A1 | 5/2008 | Harlow et al. |
| 2008/0114370 A1 | 5/2008 | Schoenefeld |
| 2008/0133022 A1 | 6/2008 | Caylor |
| 2008/0140081 A1 | 6/2008 | Heavener et al. |
| 2008/0140209 A1 | 6/2008 | Iannotti et al. |
| 2008/0140213 A1 | 6/2008 | Ammann et al. |
| 2008/0146969 A1 | 6/2008 | Kurtz |
| 2008/0147072 A1 | 6/2008 | Park et al. |
| 2008/0147073 A1 | 6/2008 | Ammann et al. |
| 2008/0161815 A1 | 7/2008 | Schoenefeld et al. |
| 2008/0161816 A1 | 7/2008 | Stevens et al. |
| 2008/0172125 A1 | 7/2008 | Ek |
| 2008/0195099 A1 | 8/2008 | Minas |

(56) References Cited

U.S. PATENT DOCUMENTS

| | | |
|---|---|---|
| 2008/0195107 A1 | 8/2008 | Cuckler et al. |
| 2008/0195108 A1 | 8/2008 | Bhatnagar et al. |
| 2008/0195109 A1 | 8/2008 | Hunter et al. |
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |
| 2008/0215059 A1 | 9/2008 | Carignan et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0255674 A1 | 10/2008 | Rahaman et al. |
| 2008/0257363 A1 | 10/2008 | Schoenefeld et al. |
| 2008/0262500 A1 | 10/2008 | Collazo |
| 2008/0262624 A1 | 10/2008 | White et al. |
| 2008/0269596 A1 | 10/2008 | Revie et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2008/0294170 A1 | 11/2008 | O'Brien |
| 2008/0294266 A1 | 11/2008 | Steinberg |
| 2008/0300600 A1 | 12/2008 | Guelat et al. |
| 2008/0306485 A1 | 12/2008 | Coon et al. |
| 2008/0306558 A1 | 12/2008 | Hakki |
| 2008/0312659 A1* | 12/2008 | Metzger et al. .............. 606/87 |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0024131 A1 | 1/2009 | Metzger et al. |
| 2009/0024169 A1 | 1/2009 | Triplett et al. |
| 2009/0043556 A1 | 2/2009 | Axelson et al. |
| 2009/0076371 A1 | 3/2009 | Lang et al. |
| 2009/0076512 A1 | 3/2009 | Ammann et al. |
| 2009/0076520 A1 | 3/2009 | Choi |
| 2009/0076555 A1 | 3/2009 | Lowry et al. |
| 2009/0082770 A1 | 3/2009 | Worner et al. |
| 2009/0082774 A1 | 3/2009 | Oti et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093815 A1 | 4/2009 | Fletcher et al. |
| 2009/0093816 A1 | 4/2009 | Roose et al. |
| 2009/0096613 A1 | 4/2009 | Westrick |
| 2009/0099567 A1 | 4/2009 | Zajac |
| 2009/0105837 A1 | 4/2009 | Lafosse et al. |
| 2009/0116621 A1 | 5/2009 | Yuan et al. |
| 2009/0118736 A1 | 5/2009 | Kreuzer |
| 2009/0118769 A1 | 5/2009 | Sixto, Jr. et al. |
| 2009/0131941 A1 | 5/2009 | Park et al. |
| 2009/0131942 A1* | 5/2009 | Aker et al. .............. 606/88 |
| 2009/0138020 A1 | 5/2009 | Park et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0209884 A1 | 8/2009 | Van Vorhis et al. |
| 2009/0209961 A1 | 8/2009 | Ferrante et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228016 A1 | 9/2009 | Alvarez et al. |
| 2009/0234360 A1 | 9/2009 | Alexander |
| 2009/0248044 A1 | 10/2009 | Amiot et al. |
| 2009/0250413 A1 | 10/2009 | Hoeppner |
| 2009/0254093 A1 | 10/2009 | White et al. |
| 2009/0254367 A1 | 10/2009 | Belcher et al. |
| 2009/0259312 A1 | 10/2009 | Shterling et al. |
| 2009/0270868 A1 | 10/2009 | Park et al. |
| 2009/0274350 A1 | 11/2009 | Pavlovskaia et al. |
| 2009/0287217 A1 | 11/2009 | Ammann et al. |
| 2009/0287309 A1 | 11/2009 | Walch et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2009/0318921 A1 | 12/2009 | White et al. |
| 2010/0010493 A1 | 1/2010 | Dower |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0036404 A1* | 2/2010 | Yi et al. .............. 606/167 |
| 2010/0042105 A1 | 2/2010 | Park et al. |
| 2010/0049195 A1 | 2/2010 | Park et al. |
| 2010/0057088 A1 | 3/2010 | Shah |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0082067 A1 | 4/2010 | Kondrashov |
| 2010/0087829 A1 | 4/2010 | Metzger et al. |
| 2010/0094295 A1 | 4/2010 | Schnieders et al. |
| 2010/0105011 A1 | 4/2010 | Karkar et al. |
| 2010/0121334 A1 | 5/2010 | Couture et al. |
| 2010/0121335 A1 | 5/2010 | Penenberg et al. |
| 2010/0137869 A1 | 6/2010 | Borja et al. |
| 2010/0137924 A1 | 6/2010 | Tuke et al. |
| 2010/0145343 A1 | 6/2010 | Johnson et al. |
| 2010/0145344 A1 | 6/2010 | Jordan et al. |
| 2010/0152782 A1 | 6/2010 | Stone et al. |
| 2010/0160917 A1 | 6/2010 | Fitz et al. |
| 2010/0168752 A1 | 7/2010 | Edwards |
| 2010/0168754 A1 | 7/2010 | Fitz et al. |
| 2010/0168857 A1 | 7/2010 | Hatch |
| 2010/0179663 A1 | 7/2010 | Steinberg |
| 2010/0185202 A1 | 7/2010 | Lester et al. |
| 2010/0191244 A1 | 7/2010 | White et al. |
| 2010/0198224 A1 | 8/2010 | Metzger et al. |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0256649 A1 | 10/2010 | Capsal et al. |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0292743 A1 | 11/2010 | Singhal et al. |
| 2010/0305574 A1 | 12/2010 | Fitz et al. |
| 2010/0318088 A1 | 12/2010 | Warne et al. |
| 2010/0324692 A1 | 12/2010 | Uthgenannt et al. |
| 2011/0004317 A1 | 1/2011 | Hacking et al. |
| 2011/0009869 A1 | 1/2011 | Marino et al. |
| 2011/0015636 A1* | 1/2011 | Katrana et al. .............. 606/87 |

(56) References Cited

U.S. PATENT DOCUMENTS

| | | |
|---|---|---|
| 2011/0015639 A1 | 1/2011 | Metzger et al. |
| 2011/0015752 A1 | 1/2011 | Meridew |
| 2011/0022049 A1 | 1/2011 | Huebner et al. |
| 2011/0029091 A1 | 2/2011 | Bojarski et al. |
| 2011/0029116 A1 | 2/2011 | Jordan et al. |
| 2011/0035012 A1 | 2/2011 | Linares |
| 2011/0040303 A1 | 2/2011 | Iannotti |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0066193 A1 | 3/2011 | Lang et al. |
| 2011/0066245 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1* | 3/2011 | Metzger et al. .................. 606/88 |
| 2011/0092804 A1 | 4/2011 | Schoenefeld et al. |
| 2011/0093086 A1 | 4/2011 | Witt et al. |
| 2011/0106254 A1 | 5/2011 | Abel et al. |
| 2011/0125264 A1 | 5/2011 | Bagga et al. |
| 2011/0130795 A1 | 6/2011 | Ball |
| 2011/0151027 A1 | 6/2011 | Clineff et al. |
| 2011/0151259 A1 | 6/2011 | Jarman-Smith et al. |
| 2011/0153025 A1 | 6/2011 | McMinn |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1* | 7/2011 | Dubeau et al. .................. 606/87 |
| 2011/0184419 A1 | 7/2011 | Meridew et al. |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0213376 A1 | 9/2011 | Maxson et al. |
| 2011/0214279 A1 | 9/2011 | Park et al. |
| 2011/0218545 A1 | 9/2011 | Catanzarite et al. |
| 2011/0224674 A1 | 9/2011 | White et al. |
| 2011/0238071 A1 | 9/2011 | Fernandez-Scoma |
| 2011/0251617 A1 | 10/2011 | Ammann et al. |
| 2011/0257657 A1 | 10/2011 | Turner et al. |
| 2011/0269100 A1 | 11/2011 | Furrer et al. |
| 2011/0275032 A1 | 11/2011 | Tardieu et al. |
| 2011/0276145 A1 | 11/2011 | Carignan et al. |
| 2011/0282473 A1 | 11/2011 | Pavlovskaia et al. |
| 2011/0295887 A1 | 12/2011 | Palmese et al. |
| 2011/0313424 A1 | 12/2011 | Bono et al. |
| 2011/0319745 A1 | 12/2011 | Frey |
| 2012/0010619 A1 | 1/2012 | Barsoum |
| 2012/0010710 A1 | 1/2012 | Frigg |
| 2012/0010711 A1 | 1/2012 | Antonyshyn et al. |
| 2012/0041445 A1 | 2/2012 | Roose et al. |
| 2012/0065640 A1 | 3/2012 | Metzger et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0089595 A1 | 4/2012 | Jaecksch |
| 2012/0101586 A1 | 4/2012 | Carson |
| 2012/0109137 A1 | 5/2012 | Iannotti et al. |
| 2012/0109138 A1 | 5/2012 | Meridew et al. |
| 2012/0109226 A1 | 5/2012 | Iannotti et al. |
| 2012/0123422 A1 | 5/2012 | Agnihotri et al. |
| 2012/0130382 A1 | 5/2012 | Iannotti et al. |
| 2012/0136365 A1 | 5/2012 | Iannotti et al. |
| 2012/0141034 A1 | 6/2012 | Iannotti et al. |
| 2012/0143197 A1 | 6/2012 | Lang et al. |
| 2012/0143267 A1 | 6/2012 | Iannotti et al. |
| 2012/0158002 A1 | 6/2012 | Carignan et al. |
| 2012/0192401 A1 | 8/2012 | Pavlovskaia et al. |
| 2012/0209276 A1 | 8/2012 | Schuster |
| 2012/0215225 A1 | 8/2012 | Philippon et al. |
| 2012/0221017 A1 | 8/2012 | Bonutti |
| 2012/0226283 A1 | 9/2012 | Meridew et al. |
| 2012/0232596 A1 | 9/2012 | Ribeiro |
| 2012/0245587 A1 | 9/2012 | Fang et al. |
| 2012/0259335 A1 | 10/2012 | Scifert et al. |
| 2012/0265208 A1 | 10/2012 | Smith |
| 2012/0271314 A1 | 10/2012 | Stemniski et al. |
| 2012/0271366 A1 | 10/2012 | Katrana et al. |
| 2012/0277751 A1 | 11/2012 | Catanzarite et al. |
| 2012/0289965 A1 | 11/2012 | Gelaude et al. |
| 2012/0296339 A1 | 11/2012 | Iannotti et al. |
| 2012/0303004 A1 | 11/2012 | Uthgenannt et al. |
| 2012/0303033 A1 | 11/2012 | Weiner et al. |
| 2012/0310399 A1 | 12/2012 | Metzger |
| 2012/0316564 A1 | 12/2012 | Serbousek et al. |
| 2012/0323246 A1 | 12/2012 | Catanzarite et al. |
| 2013/0001121 A1 | 1/2013 | Metzger |
| 2013/0006250 A1 | 1/2013 | Metzger et al. |
| 2013/0035766 A1 | 2/2013 | Meridew |
| 2013/0046310 A1 | 2/2013 | Ranawat et al. |
| 2013/0060253 A1 | 3/2013 | Couture et al. |
| 2013/0085500 A1 | 4/2013 | Meridew et al. |
| 2013/0123850 A1 | 5/2013 | Schoenefeld et al. |
| 2013/0144392 A1 | 6/2013 | Hughes |
| 2013/0197528 A1 | 8/2013 | Zakaria et al. |
| 2013/0197687 A1 | 8/2013 | Pavlovskaia et al. |
| 2013/0218163 A1 | 8/2013 | Frey |
| 2013/0289730 A1 | 10/2013 | Gabriel et al. |
| 2014/0005672 A1 | 1/2014 | Edwards et al. |
| 2014/0052270 A1 | 2/2014 | Witt et al. |
| 2014/0081275 A1 | 3/2014 | Metzger et al. |
| 2014/0088724 A1 | 3/2014 | Meridew |
| 2014/0094816 A1 | 4/2014 | White et al. |
| 2014/0100578 A1 | 4/2014 | Metzger et al. |
| 2014/0107651 A1 | 4/2014 | Meridew et al. |
| 2014/0107654 A1 | 4/2014 | Kehres et al. |
| 2014/0107715 A1 | 4/2014 | Heilman et al. |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| DE | 3447365 A1 | 7/1986 |
| DE | 04219939 A1 | 12/1993 |
| DE | 4421153 A1 | 12/1995 |
| DE | 102009028503 A1 | 2/2011 |
| DE | 102011082902 A1 | 3/2012 |
| DE | 102012205820 A1 | 10/2012 |
| DE | 112010003901 T5 | 11/2012 |
| EP | 0114505 A1 | 8/1984 |
| EP | 0326768 A2 | 8/1989 |
| EP | 0579868 A2 | 1/1994 |
| EP | 0591985 A1 | 4/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 01486900 A1 | 2/2004 |
| EP | 1437102 A1 | 7/2004 |
| EP | 1634551 A2 | 3/2006 |
| EP | 1852072 A2 | 7/2007 |
| EP | 1832239 A1 | 9/2007 |
| EP | 2029061 A2 | 3/2009 |
| EP | 2168507 A2 | 3/2010 |
| EP | 2303146 A1 | 4/2011 |
| EP | 2303192 A1 | 4/2011 |
| EP | 2352445 A1 | 8/2011 |
| EP | 2396741 A1 | 12/2011 |
| EP | 2398381 A1 | 12/2011 |
| EP | 2403437 A2 | 1/2012 |
| EP | 2491873 A2 | 8/2012 |
| EP | 2502582 A1 | 9/2012 |

(56) References Cited

FOREIGN PATENT DOCUMENTS

| | | |
|---|---|---|
| EP | 2709568 A1 | 3/2014 |
| FR | 2659226 A1 | 9/1991 |
| FR | 2721195 A1 | 12/1995 |
| FR | 2768916 A1 | 4/1999 |
| GB | 2094590 A | 9/1982 |
| GB | 2197790 A | 6/1988 |
| GB | 2442441 A | 4/2008 |
| GB | 2447702 A | 9/2008 |
| GB | 2483980 A | 3/2012 |
| GB | 2486390 A | 6/2012 |
| GB | 2490220 A | 10/2012 |
| GB | 2491526 A | 12/2012 |
| JP | 59157715 A | 9/1984 |
| JP | 60231208 A | 1/1985 |
| JP | 6-233790 A | 8/1994 |
| JP | 2000245758 A | 9/2000 |
| JP | 2009514612 A | 4/2009 |
| JP | 2011505080 A | 2/2011 |
| JP | 2011527885 A | 11/2011 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| TW | 231755 | 5/2005 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0296268 A2 | 2/2002 |
| WO | WO-0217821 A2 | 3/2002 |
| WO | WO-0226145 | 4/2002 |
| WO | WO-0236024 A1 | 5/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051239 A1 | 6/2005 |
| WO | WO-2005051240 A1 | 6/2005 |
| WO | WO-2005077039 A2 | 8/2005 |
| WO | WO-2006127486 A2 | 1/2006 |
| WO | WO-2006058057 A2 | 6/2006 |
| WO | WO-2006060795 A1 | 6/2006 |
| WO | WO-2006092600 A1 | 9/2006 |
| WO | WO-2006134345 A1 | 12/2006 |
| WO | WO-2006136955 A1 | 12/2006 |
| WO | WO-2007137327 A1 | 2/2007 |
| WO | WO-2007041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008091358 A1 | 7/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010093902 A1 | 8/2010 |
| WO | WO-2010096553 A1 | 8/2010 |
| WO | WO-2010096557 A2 | 8/2010 |
| WO | WO-2010124164 A1 | 10/2010 |
| WO | WO-2010129870 A1 | 11/2010 |
| WO | WO-2010144705 A1 | 12/2010 |
| WO | WO-2010148103 A1 | 12/2010 |
| WO | WO-2011018458 A1 | 2/2011 |
| WO | WO-2011041398 A1 | 4/2011 |
| WO | WO-2011060536 A1 | 5/2011 |
| WO | WO-2011019797 A3 | 7/2011 |
| WO | WO-2011106711 A1 | 9/2011 |
| WO | WO-2011109260 A1 | 9/2011 |
| WO | WO-2011110374 A1 | 9/2011 |
| WO | WO-2012006444 A2 | 1/2012 |
| WO | WO-2012033821 A1 | 3/2012 |
| WO | WO-2012058344 A1 | 5/2012 |
| WO | WO-2012061042 A1 | 5/2012 |
| WO | WO-2012058353 A4 | 6/2012 |
| WO | WO-2012058355 A4 | 7/2012 |
| WO | WO-2012058349 A4 | 8/2012 |
| WO | WO-2012116206 A1 | 8/2012 |
| WO | WO-2012158917 A1 | 11/2012 |
| WO | WO-2012173929 A1 | 12/2012 |
| WO | WO-2012174008 A1 | 12/2012 |

OTHER PUBLICATIONS

"Ascent Total Knee System," brochure. Biomet, Inc. (1999) 16 sheets.

"Customized Patient Instruments, Patient specific instruments for patient specific needs," brochure. (2008) DePuy Orthopaedics, Inc. 14 sheets.

"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.

"Discovery® Elbow System Surgical Technique," brochure. Biomet Orthopedics, Inc. (2008) pp. 1-25.

"Discovery® Elbow System," brochure. Biomet Orthopedics, Inc. (2007) 3 sheets.

"Hipsextant Instructions of Use." (2011) Surgical Planning Associates, Inc. 19 pages.

"Knee tensor combined with laser femoral head locator," Research Disclosure. Jul. 2006. No. 507; p. 903.

"Method for constructing an allograft sleeve." Research Disclosure (Dec. 2003) No. 476, p. 1294.

"OSS™ Orthopaedic Salvage System, Femoral/Tibial Augmentation," brochure. Biomet Orthopedics, Inc., (2003) pp. 1-8 (12 sheets).

"Patient Matched PMI Implants, C.A.M.R.A. 3-D Imaging," brochure, Biomet, Inc. (1990) 6 pages.

"Regenerex® Tibial Cone Augment, Surgical Technique Addendum to the Vanguard® SSK Revision System," brochure. Biomete® Orthopedics. (2009) pp. 1-8 (12 sheets).

"Signature™ Personalized Patient Care, Surgical Technique Addendum to the Vanguard Knee System" brochure. Biomete® Orthopedics, Inc. (2009) pp. 1-8.

"TruMatch™ Personalized knee replacement solutions," tri-fold brochure. (2009) SIGMA® DePuy Orthopaedics, Inc. 2 pages.

"Vanguard® PFR Partial Knee Patellofemoral Replacement System," Surgical Technique brochure. Biomet Orthopaedics, (2010) pp. 1-25.

"Zimmer® UniSpacer® Knee System," brochure. (2005) Zimmer, Inc. 4 sheets.

Birnbaum, Klaus, M.D., "Computer-Assisted Orthopedic Surgery With Individual Templates and Comparison to Conventional Method," SPINE vol. 26, No. 4, pp. 365-370 (2001) Lippincott Williams & Wilkins, Inc.

Botha, Cheri P., Technical Report: DeVIDE—The Delft Visualisation and Image processing Development Environment, pp. 1-49 (May 31, 2006).

Cohen, Zohara A., et al. "Knee cartilage topography, thickness, and contact areas from MRI: in-vitro calibration and in-vivo measure-

(56) References Cited

OTHER PUBLICATIONS ments." Journal of the OsteoArthritis Research Society International. Osteoarthritis and Cartilage, (1999) vol. 7; No. 1 pp. 95-109.
Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.
Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.
Haaker, R.G., et al., "Minimal-invasive navigiert implantierte unikondyläre Knieendoprothese", Orthopäde 2006 35:1073-1079 (2006) Spinger Medizin Verlag.
Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.
Hazan, Eric J., M.D., "Computer-Assisted Orthopaedic Sugery, A New Paradigm," Techniques in Orthopaedics® vol. 8, No. 2, (2003) pp. 221-229.
Hutmacher, Dietmar, W., "Scaffolds in tissue engineering bone and cartilage," Biomaterials, 2000 Elsevier Science Ltd. (pp. 2529-2543).
International Preliminary Report on Patentability and Written Opinion for PCT/US2009/039578 mailed Oct. 28, 2010 claiming benefit of U.S. Appl. No. 12/103,834, filed Apr. 16, 2008.
International Preliminary Report on Patentability and Written Opinion mailed Oct. 28, 2010 for PCT/US2009/039507 claiming benefit of U.S. Appl. No. 12/103,824, filed Apr. 16, 2008.
International Preliminary Report on Patentability for PCT/US2007/013223 mailed Dec. 24, 2008 claiming benefit of U.S. Appl. No. 11/756,057, filed May 31, 2007.
International Preliminary Report on Patentability mailed Mar. 31, 2011 for PCT/US2009/056670 claiming benefit of U.S. Appl. No. 12/211,407, filed Sep. 16, 2008.
International Search Report and Written Opinion for PCT/US2007/013223 mailed Nov. 26, 2007, claiming benefit of U.S. Appl. No. 11/756,057, filed May 31, 2007.
International Search Report and Written Opinion for PCT/US2009/039507 mailed Jul. 14, 2009, claiming benefit of U.S. Appl. No. 12/103,824.
International Search Report and Written Opinion for PCT/US2009/056670 mailed Mar. 2, 2010 claiming benefit of U.S. Appl. No. 12/211,407, filed Sep. 16, 2008.
International Search Report and Written Opinion mailed Apr. 22, 2010 for PCT/US2010/024579 claiming benefit of U.S. Appl. No. 12/389,930, filed Feb. 20, 2009.
International Search Report and Written Opinion mailed Aug. 19, 2010 for PCT/US2010/024584 claiming benefit of U.S. Appl. No. 12/389,901, filed Feb. 20, 2009.
International Search Report and Written Opinion mailed Dec. 7, 2010 for PCT/US2010/050701 claiming benefit of U.S. Appl. No. 12/571,969, filed Oct. 1, 2009.
International Search Report and Written Opinion mailed Jul. 31, 2009 for PCT/US2009/039578 claiming benefit of U.S. Appl. No. 12/103,834, filed Apr. 16, 2008.
International Search Report and Written Opinion mailed Jun. 10, 2010 for PCT/US2010/038177 claiming benefit of U.S. Appl. No. 12/483,807, filed Jun. 12, 2009.
International Search Report and Written Opinion mailed Jun. 4, 2010 for PCT/US2010/024073 filed Feb. 12, 2010, claiming benefit of U.S. Appl. No. 12/371,096, filed Feb. 13, 2009.
International Search Report and Written Opinion mailed May 9, 2011 for PCT/US2011/026412 claiming benefit of U.S. Appl. No. 12/872,663, filed Aug. 31, 2010.
International Search Report and Written Opinion mailed Oct. 5, 2010 for PCT/US2010/038845 claiming benefit of U.S. Appl. No. 12/486,992, filed Jun. 18, 2009.
Invitation to Pay Additional Fees mailed May 3, 2011 for PCT/US2011/026333 claiming benefit of U.S. Appl. No. 12/714,023, filed Feb. 26, 2010.
Invitation to Pay Additional Fees with Partial International Search mailed Nov. 26, 2009 for PCT/US2009/056670.
Kaus, Michael R., Ph.D., "Automated Segmentation of MR Images of Brain Tumors," Radiology, vol. 218, No. 2, (2001) pp. 586-591.
Kelly, Todd C., M.D., "Role of Navigation in Total Hip Arthroplasty." The Journal of Bone & Joint Surgery(2009) pp. 153-158. vol. 91-A, Supplement 1.
Klein, M., "Robot assisted insertion of craniofacial implants—clinical experience," CARS 2001, pp. 133-138 (2001) Elsevier Science B.V.
Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.
Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.
Murphy, S.B., et al. "The Hip Sextant: Navigation of Acetabular Component Orientation Using a Mechanical Instrument," brochure. (2009) 1 page.
Nicholls, Paul, M.D., "Trauma Grand Rounds PMI (Patient-Matched Implants)" brochure, Biomet Orthopedics, Inc., (Feb. 29, 2000) 1 page.
Overhoff, H.M., et al., "Total Knee Arthroplasty: Coordinate System Definition and Planning based on 3-D Ultrasound Image Volumes," CARS 2001, pp. 283-288, (2001) Elsevier Science B.V.
Portheine, F., "CT-basierte Planung und DISOS-Schablonennavigation in der Kniegelenkendoprothetik," in Navigation und Robotic in der Gelenk—und Wirbelsäulenchirugie, Kapitel 32, Springer Verlag (2003) pp. 262-269.
Portheine, F., et al., Entwicklung eines klinischen Demonstrators für die computerunterstützte Orthopädische Chirurgie mit CT-Bildbasierten Individualschablonen, Bildverarbeitung fur die Medizin (1998) 5 pages.
Portheine, K., "Development of a clinical demonstrator for computer assisted orthopedic surgery with CT-image based individual templates," Computer Assisted Radiology and Surgery, pp. 944-949, (1997) Elsevier Science B.V.
Radermacher, "Computer Assisted Orthopaedic Surgery with Image Based Individual Templates," Clinical Orthopaedics and Related Research No. 354, pp. 28-38 (1998) Lippincott Williams & Wilkins.
Radermacher, K., et al., "Computer Integrated Orthopaedic Surgery: Connection of Planning and Execution in Surgical Intervention," Computer-integrated surgery: technology and clinical applications, (1996) pp. 451-463.
Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.
Radermacher, K., et al., "Image Guided Orthopedic Surgery Using Individual Templates," Springer Berlin/Heidelberg, CVRMed-MRCAS'97, vol. 1205/1997 pp. 606-615).
Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.
Radermacher, Klaus, et al. "Computer Assisted Orthopaedic Individual Templates." Clinical Orthopaedics and Related Research. (Sep. 1998) No. 354; pp. 28-38.
Schuller-Götzburg, P., et al., 3D-Implantatplanung und Stereolithographie-Implantatbohrschablonen, Stomatologie 101.3, pp. 55-59 (2004).
Sharp, S. Michael, Ph.D., Patient-Specific, Resurfacing Bi-Compartmental Arthruroplasty, Futuretech, Orthopaedic Product News (Mar./Apr. 2008) pp. 12-15.
Sisto, Domenick, J., et al., "Custom Patellofemoral Arthroplasty of the Knee Surgical Technique," Journal of Bone and Joint Surgery, vol. 89-A, pp. 214-225 (2007).

(56) References Cited

OTHER PUBLICATIONS

Slammin, John et al, "Do You Have This Implant in My Size?", MDT Medical Design Technology, 3 pages, http://www.mdtmag.com/scripts/ShowPR.asp?PUBCODE=046&ACCT=0007796&ISSUE . . . accessed Jul. 31, 2008.

Steinwachs, Matthias Reinhard, "Cartilage Repair—Autologous Chondrocyte Transplantation and Autologous Matrix-induced Chondrogenesis," European Musculoskeletal Review (2006) pp. 65-68.

"Comprehensive® Reverse Shoulder System Surgical Technique," Biomet Orthopedics brochure (2009-2012), 48 pages.

"Comprehensive® Reverse Shoulder System Technical Design Features," Biomet Orthopedics brochure (2009), 3 pages.

"Comprehensive® Reverse Shoulder System," Biomet Orthopedics brochure (2009), 8 pages.

"Comprehensive® Shoulder System Surgical Technique," Biomet Orthopedics brochure (2007), pp. 1-53.

"Comprehensive® Total Shoulder System," Biomet Orthopedics brochure (2011), 4 pages.

Friedman, R.J. et al., "The Use of Computerized Tomography in The Measurement of Glenoid Version", Journal of Bone & Joint Surgery Am. (JBJS) 1992;74:1032-1037 (Aug. 1992).

International Search Report and Written Opinion mailed Dec. 18, 2012 for PCT/US2012/059189, which claims benefit of U.S. Appl. No. 13/597,478, filed Aug. 29, 2011.

International Search Report and Written Opinion mailed Feb. 6, 2013 for PCT/US2012/060842, which claims benefit of U.S. Appl. No. 13/653,868, filed Oct. 17, 2012.

International Search Report and Written Opinion mailed Feb. 6, 2013 for PCT/US2012/060854, which claims benefit of U.S. Appl. No. 13/653,893, filed Oct. 17, 2012.

International Search Report and Written Opinion mailed Nov. 15, 2012, for PCT/US2012/052853, which claims benefit of U.S. Appl. No. 13/221,968, filed Aug. 31, 2011.

International Search Report mailed Oct. 23, 2012, for PCT/US2012/041893, which claims benefit of U.S. Appl. No. 61/496,177, filed Jun. 13, 2011.

Invitation to Pay Additional Fees mailed Feb. 6, 2013 for PCT/US2012/060848, which claims benefit of U.S. Appl. No. 13/653,878, filed Oct. 17, 2012.

Invitation to Pay Additional Fees mailed Feb. 7, 2013 for PCT/US2012/060853, which claims benefit of U.S. Appl. No. 13/653,893, filed Oct. 17, 2012.

International Search Report and Written Opinion for PCT/US2013/026875 mailed Jun. 7, 2013, claiming benefit of U.S. Appl. No. 13/400,652, filed Feb. 21, 2012.

International Preliminary Report on Patentability dated Sep. 6, 2013 for PCT/US2012/026356, claiming benefit of U.S. Appl. No. 13/041,883, filed Mar. 7, 2011.

International Preliminary Report on Patentability mailed Aug. 25, 2011 for PCT/US2010/024073 filed Feb. 12, 2010, claiming benefit of U.S. Appl. No. 12/371,096, filed Feb. 13, 2009.

International Preliminary Report on Patentability mailed Sep. 1, 2011 for PCT/US2010/024579 claiming benefit of U.S. Appl. No. 12/389,930, filed Feb. 20, 2009.

International Preliminary Report on Patentability mailed Sep. 1, 2011 for PCT/US2010/024584 claiming benefit of U.S. Appl. No. 12/389,901, filed Feb. 20, 2009.

International Search Report and Written Opinion mailed Aug. 9, 2011 for PCT/US2011/026333 claiming benefit of U.S. Appl. No. 12/714,023, filed Feb. 26, 2010.

Biomet "Oxford® Partial Knee" brochure, 8 pages (Feb. 2011).

Biomet "The Oxford® Partial Knee Surgical Technique," brochure, pp. 1-38, (Feb. 2010).

Biomet, "Oxford® Partial Knee Microplasty® Instrumentation Surgical Technique", brochure, pp. 1-54 (May 2011).

International Preliminary Report on Patentability and Written Opinion mailed Sep. 7, 2012 for PCT/US2011/026333 claiming benefit of U.S. Appl. No. 12/714,023, filed Feb. 26, 2010.

International Preliminary Report on Patentability for PCT/US2010/050701 mailed Apr. 12, 2012 claiming benefit of U.S. Appl. No. 12/571,969, filed Oct. 1, 2009.

International Search Report and Written Opinion mailed Mar. 5, 2012 for PCT/US2011/057300 claiming benefit of U.S. Appl. No. 12/938,905, filed Nov. 3, 2010.

International Search Report and Written Opinion mailed May 8, 2012 for PCT/US2012/026356 claiming benefit of U.S. Appl. No. 13/041,883, filed Mar. 7, 2011.

Thoma, W., et al., "Endoprothetischen Versorgung des Kniegelenks auf der Basis eines 3D-computertomographischen Subtraktionsverfahrens," Zuma Thema: Computergestützte orthopädische Chirugie, Der Orthopäde 29:641-644 Springer-Verlag (Jul. 2000) Translation provided: Thoma, W., "Endoprosthetic care of the knee joint based on a 3D computer chromatography subtraction process," Topic: Computer-aided orthopedic surgery. Orthopedist 2000 29:641-644 Springer Verlag (Jul. 2000).

Great Britain Search Report mailed Dec. 21, 2011 for GB1116054.6, claiming benefit of U.S. Appl. No. 12/888,005, filed Sep. 22, 2010.

International Preliminary Report and Written Opinion mailed Jan. 5, 2012 for PCT/US2010/038845 claiming benefit of U.S. Appl. No. 12/486,992, filed Jun. 18, 2009.

International Preliminary Report on Patentability and Written Opinion mailed Dec. 22, 2011 for PCT/US2010/038177 claiming benefit of U.S. Appl. No. 12/483,807, filed Jun. 12, 2009.

International Search Report mailed Nov. 30, 2010 for PCT/EP2010/061630 filed Aug. 10, 2010 claiming benefit of DE102009028503.2 filed Aug. 13, 2009.

Supplementary European Search Report mailed Nov. 15, 2011 for EP07809326, which claims benefit of PCT/US2007/013223, filed Jun. 5, 2007; which claims priority to U.S. Appl. No. 11/756,057, filed May 31, 2007.

International Search Report and Written Opinion mailed Oct. 14, 2013 for PCT/US2013/057097 claiming benefit of U.S. Appl. No. 13/597,478, filed Aug. 29, 2012.

International Preliminary Report on Patentability and Written Opinion mailed Jan. 3, 2014 for PCT/US2012/042081 claiming benefit of U.S. Appl. No. 13/493,509, filed Jun. 11, 2012.

International Preliminary Report on Patentability and Written Opinion mailed Apr. 24, 2014 for PCT/US2012/059189 claiming benefit of U.S. Appl. No. 13/597,478, filed Aug. 29, 2012.

International Preliminary Report on Patentability and Written Opinion mailed Mar. 13, 2014 for PCT/US2012/052853 claiming benefit of U.S. Appl. No. 13/221,968, filed Aug. 31, 2011.

International Search Report and Written Opinion mailed Apr. 14, 2014 for PCT/US2013/067505 claiming benefit of U.S. Appl. No. 13/718,129, filed Dec. 18, 2012.

Invitation to Pay Additional Fees mailed Feb. 6, 2014 for PCT/US2013/067505, which claims benefit of U.S. Appl. No. 13/718,129, filed Dec. 18, 2012.

\* cited by examiner

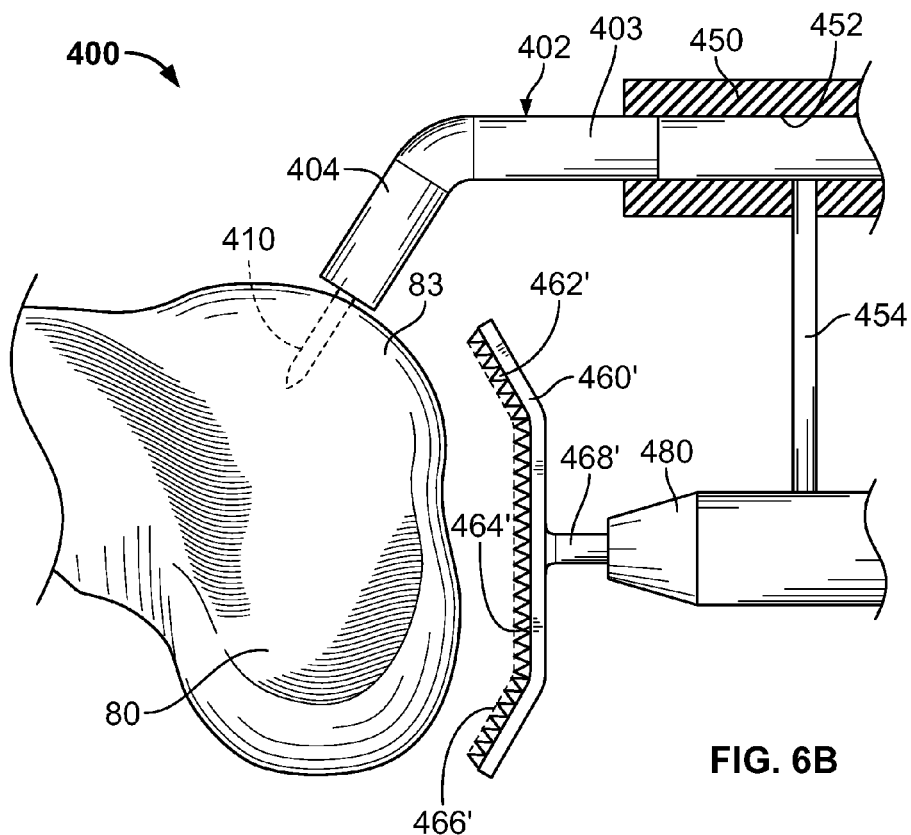
FIG. 6B
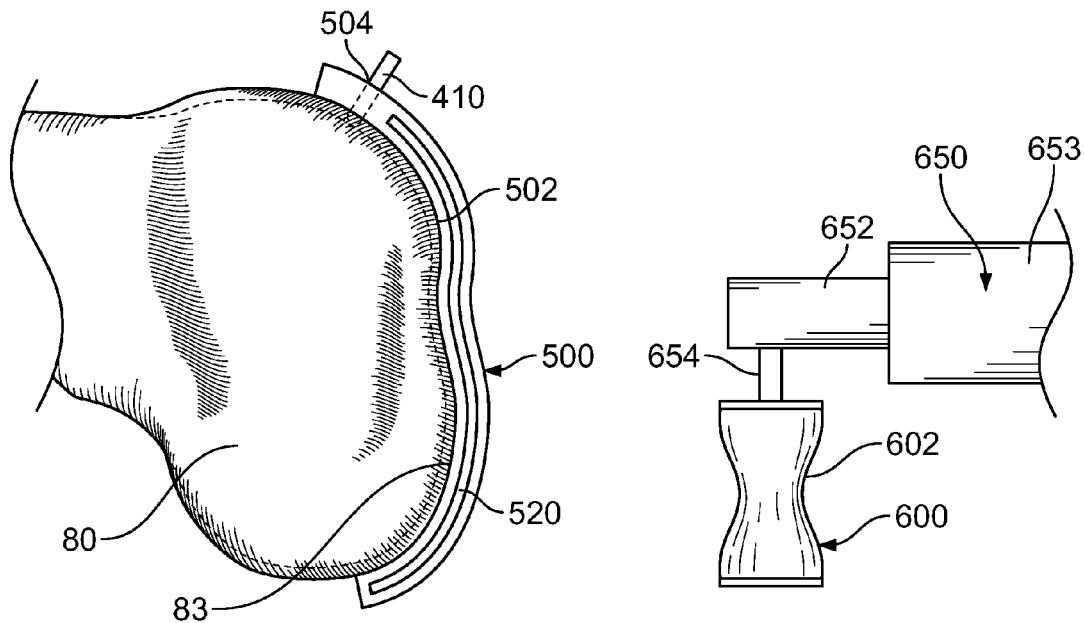
FIG. 7
FIG. 8

PATIENT-SPECIFIC BONE-CUTTING GUIDANCE INSTRUMENTS AND METHODS

INTRODUCTION

The present teachings provide various patient-specific guides and other instruments for guiding a cutting device to remove a small layer of cartilage and/or bone of a joint of a patient or otherwise prepare the bone for a patient-specific resurfacing implant. The present teachings also provide patient-specific guides for guiding a tool to prepare a bone for a non-custom implant. The patient-specific guides are designed and constructed preoperatively based on three-dimensional digital images of the patient's joint. The digital images of the patient's joint can be reconstructed from medical scans of the patient using commercially available CAD (Computer Aided Design) and/or other imaging software.

SUMMARY

The present teachings provide various orthopedic devices and associated methods for cutting or resurfacing an outer bone surface of a bone of a patient.

In some embodiments, the orthopedic device includes first and second resurfacing guides. Each resurfacing guide has a patient-specific surface preoperatively configured as a negative surface of a portion of the outer bone surface of the bone and a plurality of elongated slots. The elongated slots of the second guide are offset relative to the elongated slots of the first guide and configured for guiding a tool to resurface the outer bone surface.

In some embodiments, the orthopedic device includes a patient-specific annular frame preoperatively configured and contoured as a negative surface of a corresponding contour of an outer bone surface of the bone and including an opening. A first patient-specific template is configured to be removably receivable in the opening of the annular frame. The first patient-specific template has a patient-specific surface preoperatively configured as a negative surface of a portion of the outer bone surface. The first patient-specific template includes a first plurality of elongated slots. A second patient-specific template can also be configured to be removably receivable in the opening of the annular frame. The second patient-specific template includes a second plurality of elongated slots configured to be offset relative to the first plurality of elongated slots.

In a related method, the outer bone surface of the bone of the patient can be resurfaced by positioning the first patient-specific guide on the outer bone surface and guiding a cutting portion of a cutting tool through each of the first plurality of elongated slots to resurface the outer bone surface under the first plurality of elongated slots. The first patient-specific guide is removed from the outer bone surface and the second patient-specific guide is positioned on the outer bone surface to resurface the outer bone surface under the second plurality of elongated slots such that the outer bone surface is contiguously resurfaced.

In some embodiments, the orthopedic device includes a patient-specific alignment guide having a patient-specific surface preoperatively configured as a negative surface of a portion of an outer bone surface of the bone. The patient-specific alignment guide includes a guiding bore configured for inserting a reference pin into the bone. The orthopedic device includes a resurfacing instrument having a removable cutting effector with a cutting surface and a guiding member. The guiding member is connected to the resurfacing instrument and configured to removably engage the reference pin and to reference the cutting surface to the outer bone surface for cutting or resurfacing after the patient-specific alignment guide is removed. In some embodiments, the cutting surface is an abrading surface configured for removing articular cartilage from the outer bone surface. In some embodiments, the cutting surface is a patient-specific surface preoperatively configured as a negative surface of a portion of the outer bone surface of the bone of the patient. In other embodiments, the cutting surface is non-custom.

In a related method, the patient-specific surface of the patient-specific alignment guide is mated on the outer bone surface and the reference pin is inserted into the bone through the guiding bore of the patient-specific alignment guide. The patient-specific alignment guide is removed without removing the reference pin. The resurfacing instrument is coupled to the reference pin to register the resurfacing instrument relative to the outer bone surface. The cutting effector is coupled to the resurfacing instrument to resurface the outer bone surface.

In some embodiments, the orthopedic device includes a patient-specific alignment guide having a patient-specific surface preoperatively configured as a negative surface of a portion of an outer bone surface of a bone of a patient. The patient-specific alignment guide has a guiding bore configured for inserting a reference pin into the bone. The orthopedic device also includes a patient-specific resurfacing guide having an opening configured to receive the reference pin after the patient-specific alignment guide is removed from the bone. The patient-specific resurfacing guide has a patient-specific surface preoperatively configured as a negative surface of the outer bone surface, and an elongated slot communicating with a side slot. The orthopedic device includes a resurfacing tool having a shaft configured to be movably coupled to the patient-specific resurfacing guide along a sagittal plane of the bone. A patient-specific resurfacing member is coupled perpendicularly to the shaft and configured to move along a coronal plane of the bone.

In some embodiments, the orthopedic device includes a physical bone model having a patient-specific surface configured to replicate an outer bone surface of a bone of a patient; and a reconfigurable resurfacing instrument. The reconfigurable resurfacing instrument includes a movable and deformable resurfacing belt and a plurality of rollers extending from adjustable elongated elements and pushing against the resurfacing belt. The elongated elements operate to deform and set the resurfacing belt to a shape that is negative surface of the patient-specific surface of the physical bone model, when the resurfacing belt is positioned on the physical bone model.

In a related method, a three-dimensional digital image of a bone of a patient is prepared from medical scans of the patient. A physical bone model having an outer surface replicating an outer bone surface of the bone of the patient is prepared from the digital image of the bone. A reconfigurable resurfacing tool is set on the physical bone model to form a patient-specific resurfacing surface negative surface to the outer bone surface using the physical bone model.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The drawings described herein are for illustrative purposes only of selected embodiments and not all possible implementations, and are not intended to limit the scope of the present disclosure.

FIG. 6B is an environmental view of another cutting tool shown with the reference pin of FIG. 5 according to the present teachings;

FIG. 7 is an environmental view of a patient-specific guide for guiding a resurfacing tool according to the present teachings;

FIG. 8 is a plan view of a resurfacing tool for use with the patient-specific guide of FIG. 7 according to the present teachings;

Corresponding reference numerals indicate corresponding parts throughout the several views of the drawings.

DESCRIPTION OF VARIOUS ASPECTS

Figure 1:
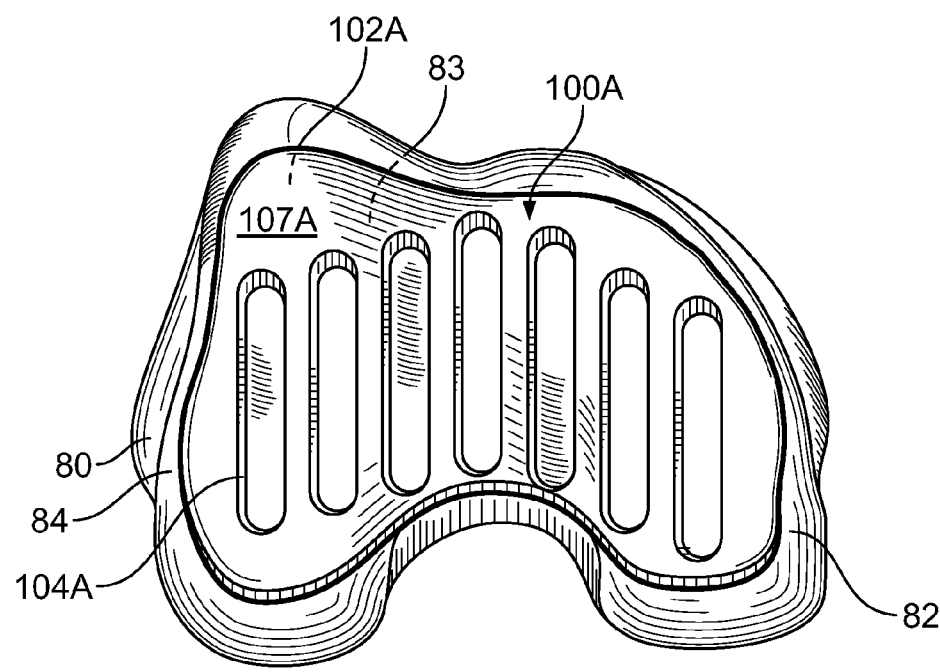
FIG. 1 is an environmental perspective view of a first patient-specific resurfacing guide according to the present teachings.

The following description is merely exemplary in nature and is in no way intended to limit the present teachings, applications, or uses. For example, although some of the present teachings are illustrated for a knee joint, the present teachings can be used for any other joint of a patient in joint arthroplasty.

The present teachings provide various patient-specific guides and other instruments for guiding a cutting device to remove a small layer of cartilage and/or bone or otherwise prepare the bone for a patient-specific resurfacing implant. The present teachings also provide patient-specific guides for guiding a tool to prepare a bone for a non-custom implant.

Various patient-specific guides, related tools and non-custom devices are illustrated in FIGS. 1-13 and discussed in detail below.

Generally, patient-specific devices, such as patient-specific guides or other instruments and/or patient-specific implants can be designed preoperatively using computer-assisted image methods based on three-dimensional images of the patient's joint and/or adjacent anatomy, as reconstructed from MRI, CT, ultrasound, X-ray, or other medical scans of the patient. Various CAD programs and/or other software can be utilized for the three-dimensional image reconstruction of the anatomy from the medical scans of the patient, such as, for example, software commercially available by Materialise USA, Plymouth, Mich.

Various pre-operative planning procedures and related patient-specific instruments are disclosed in commonly assigned and co-pending U.S. patent application Ser. No. 11/756,057, filed May 31, 2007; U.S. patent application Ser. No. 11/971,390, filed on Jan. 9, 2008; U.S. patent application Ser. No. 12/025,414, filed on Feb. 4, 2008; U.S. patent application Ser. No. 12/039,849 filed on Feb. 29, 2008; U.S. patent application Ser. No. 12/103,824, filed Apr. 16, 2008; U.S. patent application Ser. No. 12/371,096, filed Feb. 13, 2009; U.S. patent application Ser. No. 12/483,807, filed Jun. 12, 2009; U.S. patent application Ser. No. 12/872,663, filed Aug. 31, 2010; U.S. patent application Ser. No. 12/973,214, filed Dec. 20, 2010; and U.S. patent application Ser. No. 12/978,069, filed Dec. 23, 2010. The disclosures of the above applications are incorporated herein by reference.

In the preoperative planning stage for joint reconstruction, resurfacing or replacement, a preoperative surgical plan is formulated for a specific patient with optional interactive input from the patient's surgeon or other medical professional. Imaging data from medical scans of the relevant anatomy of the patient can be obtained at a medical facility or doctor's office, using any of the medical imaging methods discussed above. The imaging data can include, for example, various medical scans of a relevant joint portion or other relevant portion of the patient's anatomy, as needed for joint or other anatomy modeling and, optionally, for determination of an implant alignment axis or for other alignment purposes. The imaging data thus obtained and other associated information can be used to construct a three-dimensional computer (digital) image of the joint or other portion of the anatomy of the patient, such as, for example, the bones of a knee joint, hip joint, shoulder joint, etc. The three-dimensional digital image of the patient's anatomy is used to formulate the preoperative surgical plan for the patient. The preoperative surgical plan includes the design and construction of patient-specific guides, instruments and/or implants or the selection of non-custom implants and instruments according to surgeon-selected methods of surgical preparation and implantation.

Generally, the patient-specific guides or other instruments (patient-specific devices, for short) of the present teachings are preoperatively configured to match the surface of a bone (with or without cartilage) of a joint of a specific patient and are generally designed and preoperatively configured using computer modeling based on the patient's reconstructed three-dimensional digital image of the patient's pelvic anatomy. A patient-specific device has a bone engagement surface that is preoperatively configured to conformingly contact and match the corresponding bone surface of the patient (with or without cartilage or other soft tissue), using the reconstructed three-dimensional digital image of the patient's joint anatomy and the computer methods discussed above. In this respect, a patient-specific device can register and nestingly mate with the corresponding bone surface (with or without articular cartilage) of the specific patient in only one position. Accordingly, the patient-specific surface is preoperatively configured as an inverse or mirror or negative or a complementary surface of an outer surface of the corresponding bone, with or without cartilage.

The three-dimensional model of the patient's anatomy can be viewed on a computer display or other electronic screen and can also be reproduced as a hard copy on film or other medium and viewed by direct or indirect or backlight illumination. The model can be sized for viewing on any appropriate screen size and may be cropped, rotated, etc., as selected by the individual (e.g., the surgeon) viewing the screen.

The patient-specific devices can be manufactured by rapid prototyping methods, such as stereolithography or other similar methods or by CNC milling, or other automated or computer-controlled machining or robotic methods. The patient-specific devices, the implants and optionally other disposable instruments can be packaged and sterilized, and forwarded in a patient- and/or surgeon-specific kit to the surgeon or the surgeon's medical facility for the corresponding orthopedic procedure.

Figure 1A:
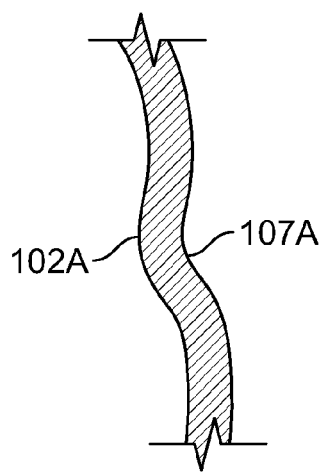
FIG. 1A is a detail of one embodiment of a patient-specific resurfacing guide according to the present teachings.
Figure 1B:
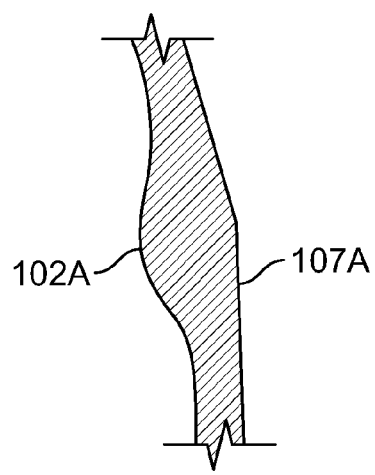
FIG. 1B is a detail of another embodiment of a patient-specific resurfacing guide according to the present teachings.
Figure 2:
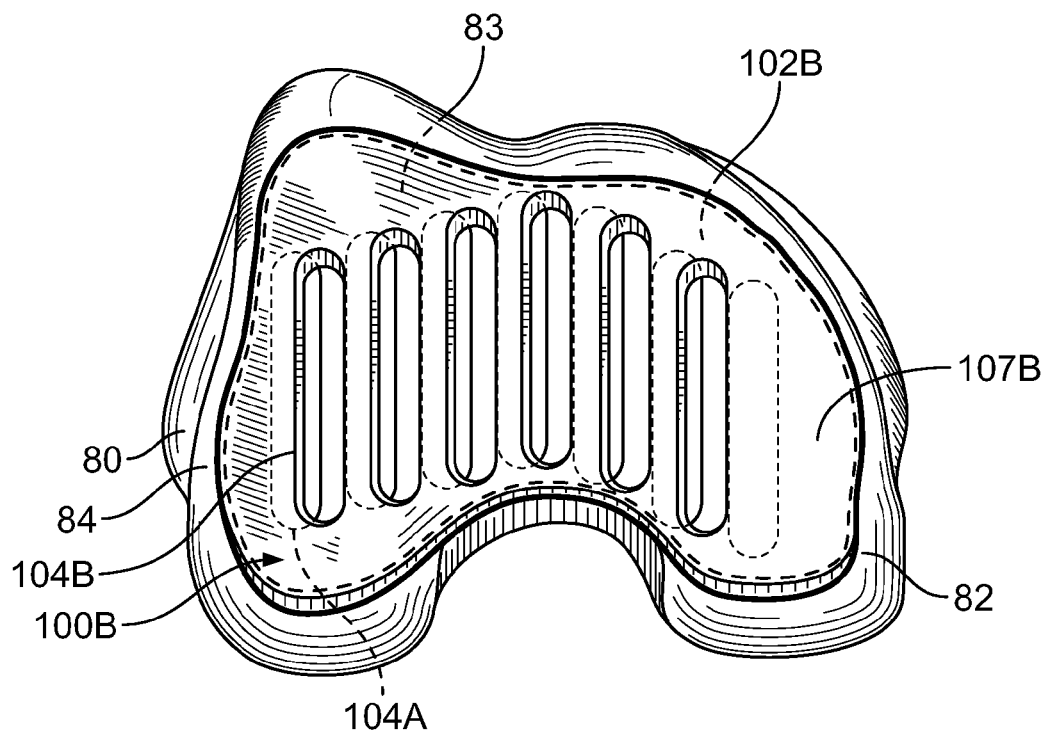
FIG. 2 is an environmental perspective view of a second patient-specific resurfacing guide according to the present teachings.

Referring to FIGS. 1 and 2, first and second patient-specific resurfacing guides 100A and 100B are illustrated for resurfacing an outer bone surface 83 of a bone 80 of a patient's joint. In this exemplary illustration, the bone 80 is shown as a distal femur of a knee joint, although the present teachings are applicable for resurfacing the bone of any other joint. Each patient-specific resurfacing guide 100A, 100B, has a first or inner patient-specific surface 102A, 102B closely mating in a complementary manner and registering with the outer bone surface 83 of the bone 80 only in one position. In other words, each first patient-specific surface 102A, 102B is preoperatively configured as an inverse or mirror or negative of the outer bone surface 83 of the bone 80 (with or without cartilage). Each patient-specific resurfacing guide 100A, 100B, has a second or outer surface 107A, 107B opposite to the first patient-specific surface 102A, 102B. Referring to FIG. 1A, the outer surface 107A, 107B can be patient-specific and parallel to the inner patient-specific surface 102A, 102B for guiding a cutting (or resurfacing) tool 200, such as the tool shown in FIG. 3, to cut or resurface the bone 80 for a patient-specific implant, i.e., such that the resurfaced outer bone surface maintains its patient-specific shape and still has the same negative surface. In some embodiments, the outer surface 107A, 107B can be non-custom, with planar surfaces for guiding the cutting tool 200 to make planar resections for engaging the planar or multi-planar inner surface of a non-custom implant, as shown in FIG. 1B. Each patient-specific resurfacing guide 100A, 100B includes a corresponding plurality of elongated slots 104A, 104B for guiding the cutting (or resurfacing) tool 200. The elongated slots 104B of the second patient-specific resurfacing guide 100B are offset and/or overlapping relative to the elongated slots 104A of the first patient-specific resurfacing guide 100A, such that the entire outer bone surface 83 of the bone 80 can be resurfaced contiguously for receiving an implant by using the first and second patient-specific resurfacing guides 100A, 100B consecutively.

Figure 3:
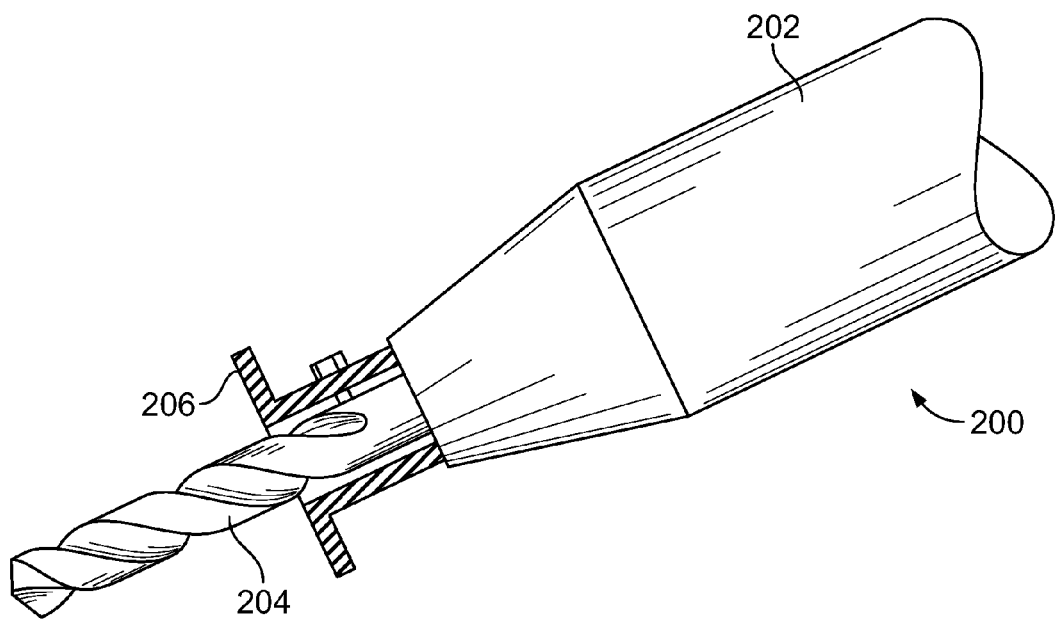
FIG. 3 is a perspective view of a resurfacing tool for use with the first and second patient-specific guides of FIGS. 1, 2 and 2A.

Referring to FIGS. 1-3, the first patient-specific resurfacing guide 100A can be registered on the bone 80 and the cutting tool 200 can be guided by the elongated slots 104A to remove cartilage (with or without removing any underlying bone) under the elongated slots 104A from the outer bone surface 83, such as, for example, from the first and second (medial or lateral) femoral condyles 82, 84 of a distal femoral bone 80. After the outer bone surface 83 under the elongated slots 104A of the first patient-specific resurfacing guide 100A has been prepared, the first patient-specific resurfacing guide 100A can be removed and the remaining cartilage or unfinished outer bone surface 83 can be finished or resurfaced either by free-hand use of the cutting tool 200 or other cutting tool or by using the second patient-specific resurfacing guide 100B. The elongated slots 104B of the second patient-specific resurfacing guide 100B overlap the location of the elongated slots 104A of the first patient-specific resurfacing guide 100A, such that the entire outer bone surface 83 can be prepared by sequentially using the cutting tool 200 through the corresponding elongated slots 104A, 104B of the first and second patient-specific resurfacing guides 100A, 100B. The patient-specific resurfacing guides 100A, 100B can also be secured on the bone 80 with pins, K-wires or other fasteners (not shown).

Figure 2A:
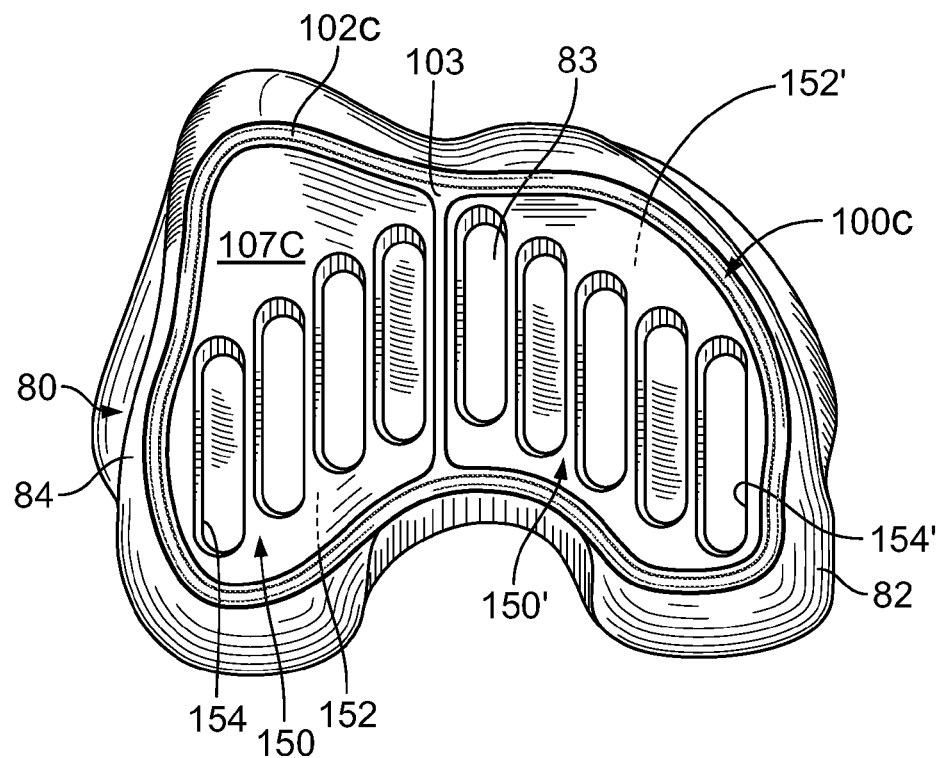
FIG. 2A is an environmental perspective view of a modular patient-specific resurfacing guide according to the present teachings.

Referring to FIG. 2A, in some embodiments, the patient-specific resurfacing guides can be modular and include of a patient-specific annular frame 100C having an opening 103 and one or more patient-specific cutting templates 150, 150' that can be received in the opening 103 and snap-fit or otherwise be removably coupled to the patient-specific annular frame 100C. The patient-specific annular frame 100C can be preoperatively contoured as a negative or mirror of the corresponding contour (or curved surface strip) of a portion of the outer bone surface 83 of the bone 80 to be resurfaced. In some embodiments, the cutting template 150 can be designed as a partial cutting template to cover only a portion of the opening 103 (partial template 150) and one or more additional partial templates 150' can be designed to be received in the remainder of the opening 103. In the exemplary illustration of FIG. 2A, two partial cutting templates 150, 150' can be positioned one adjacent to the other to occupy the opening 103, although a single cutting template can be also used for the entire opening 103. The patient-specific annular frame 100C can include a first or inner patient-specific bone engagement surface 102C that can register in only bone position on the outer bone surface 83 and an opposite (outer or second) surface 107C that can be either patient-specific and parallel to the inner patient-specific surface 102C or non-patient-specific with planar or multiplanar portions as discussed above. The patient-specific cutting templates 150, 150' can also include corresponding patient-specific bone engagement surface 152, 152' that register in only bone position on the outer bone surface 83. Each of the patient-specific surfaces 152, 152' is preoperatively configured as an inverse or mirror or negative of outer bone surface 83, with or without cartilage.

The patient-specific cutting templates 150, 150' can include a plurality of elongated slots 154, 154' for guiding a tool, such as the cutting tool 200 shown in FIG. 3. Each patient-specific cutting template 150, 150' can be removed and replaced with a similar second template having elongated slots that are offset and/or overlap relative to the slots 154, 154', as discussed above in connection with unitary patient-specific resurfacing guides 100A, 100B. In some embodiments, a plurality (two or more) of partial cutting templates similar to the templates 150, 150' can be used. In some embodiments, one or more partial cutting templates 150, 150' can slide in the medial-lateral direction by a small offset, such that the outer bone surface 83 under the corresponding partial cutting template 150, 150' can be resurfaced for receiving an implant without using additional partial templates with offset elongated slots relative to the elongated slots 154, 154'. A slidable partial cutting template can have a mediolateral dimension that is sufficiently small such that it can slide relative to the outer bone surface 83 while having a substantially patent-specific surface. The patient-specific annular frame 100C and, optionally, the patient-specific cutting templates 150, 150' can be secured on the bone 80 with pins, K-wires or other fasteners (not shown).

Referring to FIG. 3, the cutting tool 200 can include a handle 202 and a cutting portion 204, such as, for example, a burr or mill cutter. The cutting tool 200 can include a depth stop 206 that can abut the outer surface 107A, 107B, opposite to the inner patient-specific surface 102A, 102B of the patient-specific resurfacing guide 100A, 100B and limit the penetration of the cutting portion 204 into the bone 80 through the corresponding elongated slots 104A, 104B. The cutting portion 204 can be preoperatively configured for removing cartilage and creating a finished or resurfaced contoured surface of the bone 80 for receiving, for example, a patient-specific implant. In other embodiments, the cutting portion 204 can also be preoperatively configured to create a planar surface for receiving a non-custom implant having a planar or multi-planar bone-engaging surface.

Figure 4:
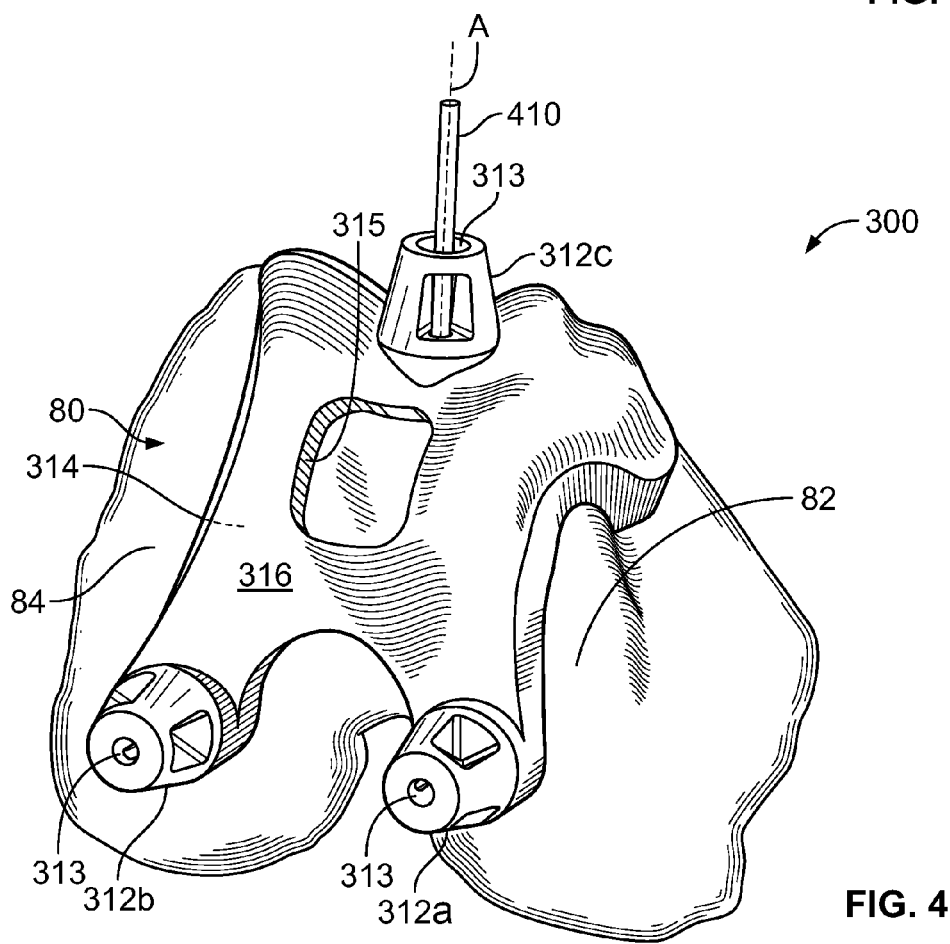
FIG. 4 is an environmental perspective view of a patient-specific guide for installing a reference pin.

Referring to FIGS. 4-6B, another bone preparation procedure and associated instruments are illustrated according to the present teachings. Briefly, a patient-specific alignment guide 300 is configured for registration (i.e., positionable by design in only one position) on the outer bone surface 83 for installing a reference pin 410 on the bone 80, as shown in FIG. 4. Patient-specific alignment guides for positioning reference or alignment pins are also disclosed in the above-referenced and incorporated herein patent applications and in commonly assigned and co-pending U.S. patent application Ser. No. 12/955,361, filed Nov. 29, 2010, and incorporated herein by reference. The reference pin 410 can be used to guide a resurfacing instrument 400 operable to remove cartilage and/or bone using a cutting surface 466 of a cutting effector 460 of the resurfacing instrument 400. The cutting surface 466 can be patient-specific, as illustrated in FIG. 6A, for removing cartilage and preparing the outer bone surface 83 for receiving a patient-specific implant. Alternatively, a cutting effector 460' with a cutting surface 466' can be coupled to the resurfacing instrument 400. The cutting effector 460' can be non-custom and configured for removing cartilage and bone and preparing planar bone faces for a non-custom implant that has a corresponding planar or multi-planar bone engaging surface.

Figure 5:
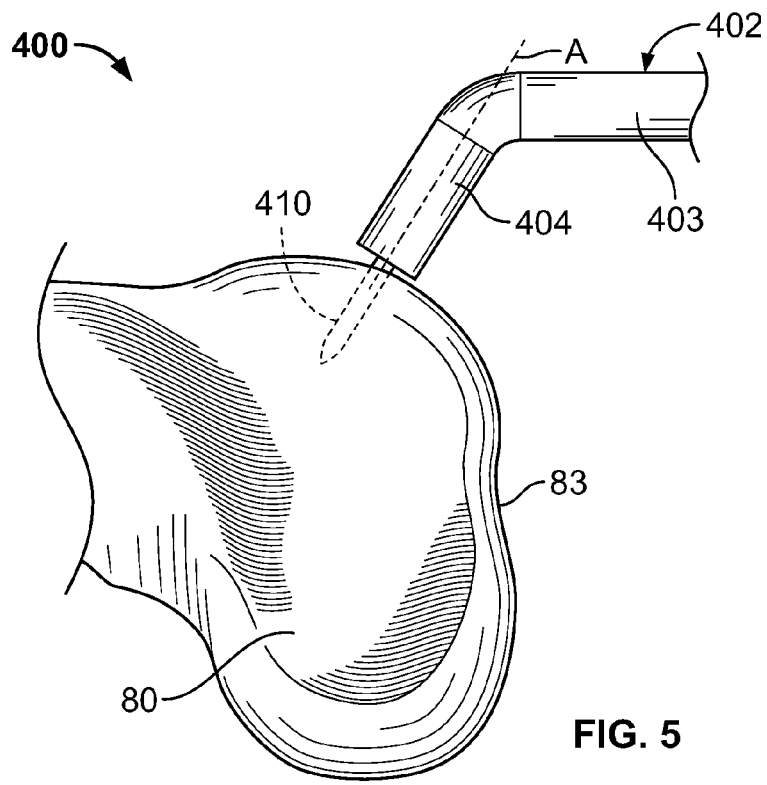
FIG. 5 is an environmental perspective view of the reference pin of FIG. 4 referencing a guide of cutting tool relative to the bone according to the present teachings.
Figure 6A:
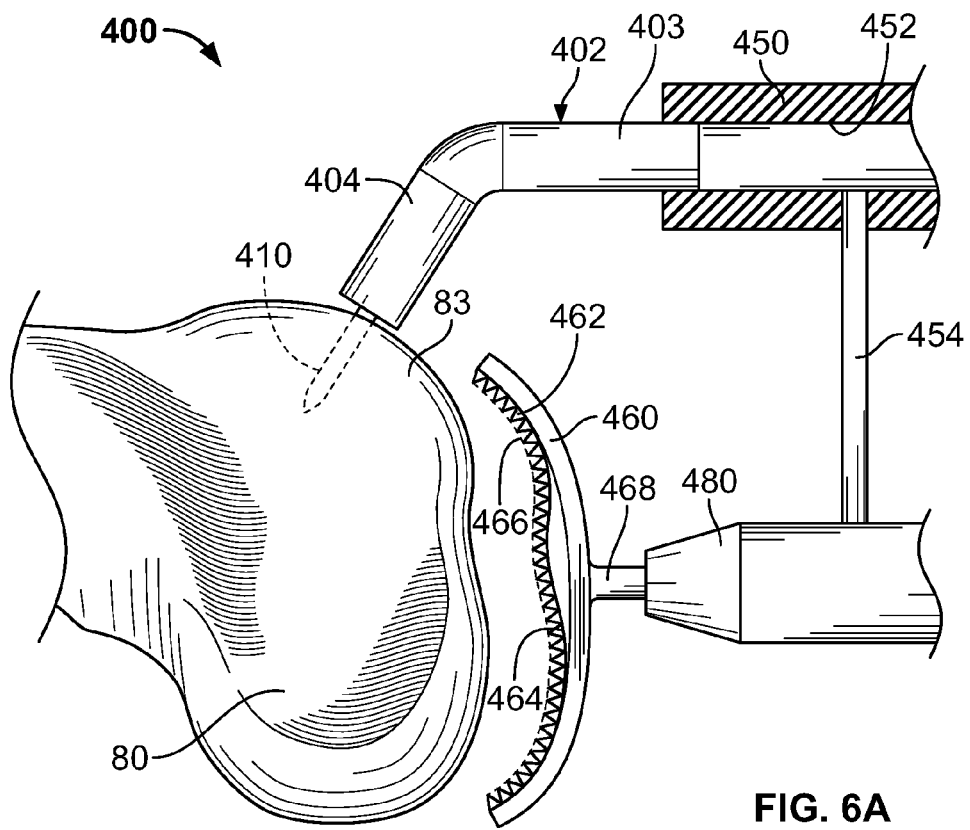
FIG. 6A is an environmental view of a patient-specific cutting tool shown with the reference pin of FIG. 5 according to the present teachings.

More specifically, and with continued reference to FIGS. 4-6B, the patient-specific alignment guide 300 can be configured preoperatively to include a patient-specific engagement surface 314 that is complementary and made to closely conform and mate (as inverse, negative or mirror surface) with a portion of the patient's bone 80 (the anterior-distal outer bone surface 83 of the patient's femur 80 in the exemplary illustration of FIG. 4) based on the pre-operative plan, as described above. The patient-specific alignment guide 300 can be lightweight and include a window/opening 315 and first and second distal guiding formations 312a, 312b defining guiding bores 313 for receiving fixation pins and/or guiding corresponding distal alignment pins (not shown). The patient-specific alignment guide 300 can also include either a pair or, as shown in FIG. 4, a single anterior guiding formation 312c defining a guiding bore 313 for guiding corresponding anterior alignment or reference pin 410 along an alignment direction A. The alignment direction A can be determined preoperatively for placing the cutting surface 466 of the resurfacing instrument 400 in a preoperatively determined position in reference to the outer bone surface 83 of the bone 80. Specifically, the reference pin 410 can be used as a guide after the patient-specific alignment guide 300 has been removed, as shown in FIGS. 5, 6A and 6B. The patient-specific alignment guide 300 can be secured on the bone 80 with pins, K-wires or other fasteners (not shown).

With continued reference to FIGS. 5, 6A and 6B, the resurfacing instrument 400 can include a curved or angled guiding member 402 with a distal portion 404 that is preoperatively configured to be aligned along the alignment direction A when the distal portion 404 is coupled to the reference pin 410. A proximal portion 403 of the guiding member 402 can be received in a bore 452 of a guide tube 450 or otherwise connected to the guide tube 450. The guide tube 450 can be coupled to a holder 480 of the resurfacing instrument 400 using a connector 454. The connector 454 can be integrally or removably coupled to the guide tube 450 and to the holder 480, such that when the guiding member 402 is coupled to the reference pin 410, the holder 480 is oriented to position the cutting effector 460 for resurfacing the outer bone surface 83 of the bone 80, as described above. The cutting effector 460 can be removably coupled to the holder 480 with a shaft 468. The cutting effector 460 can be, for example, a vibratory cutter, as illustrated in FIGS. 6A and 6B, or a cutter with a burr or milling head or other type of cutting tool, including, for example, the resurfacing member 600 shown in FIG. 8, and discussed below in relation to another embodiment illustrated in FIGS. 7-9. The cutting effector 460 can be operated through a connection to an external power source or to internal power source (battery).

In the illustrative embodiment of FIG. 6A, the cutting effector 460 can include a patient-specific support surface 464 preoperatively configured to mirror (as a negative or inverse surface) the outer bone surface 83 (or portion thereof) of the bone 80 to be resurfaced. The patient-specific support surface 464 can be a supporting surface coupled to grinding (or cutting) elements 462. In the patient-specific embodiment of FIG. 6A, the endpoints of the grinding elements 462 can form a patient-specific cutting surface 466 parallel to patient-specific support surface 464 and mirroring (negative or inverse surface) the outer bone surface 83 for removing cartilage. Although the grinding elements 462 are shown in exaggeration as teeth, in the embodiment of FIG. 6A the grinding elements 462 can be grit-like and attached to the patient-specific support surface 464. A suction device (not shown) can be also attached to the holder 480 and provide suction to remove the cartilage particles or other resurfacing debris through a bore of the shaft 468.

Referring to FIG. 6B, the non-custom cutting effector 460' can be removably coupled to the holder 480 via a shaft 468'. The cutting effector 460' can include a planar or piecewise planar (multi-planar) support surface 464' that includes cutting elements 462' in the form of cutting teeth or cutting blade elements. The cutting elements 462' can form a cutting surface 466' parallel to the support surface 464' and can cut planar surfaces through the bone 80 corresponding to the planes of the support surface 464', removing both cartilage and bone material for preparing the outer bone surface 83 for a non-custom implant having planar bone engaging interior faces.

Figure 9:
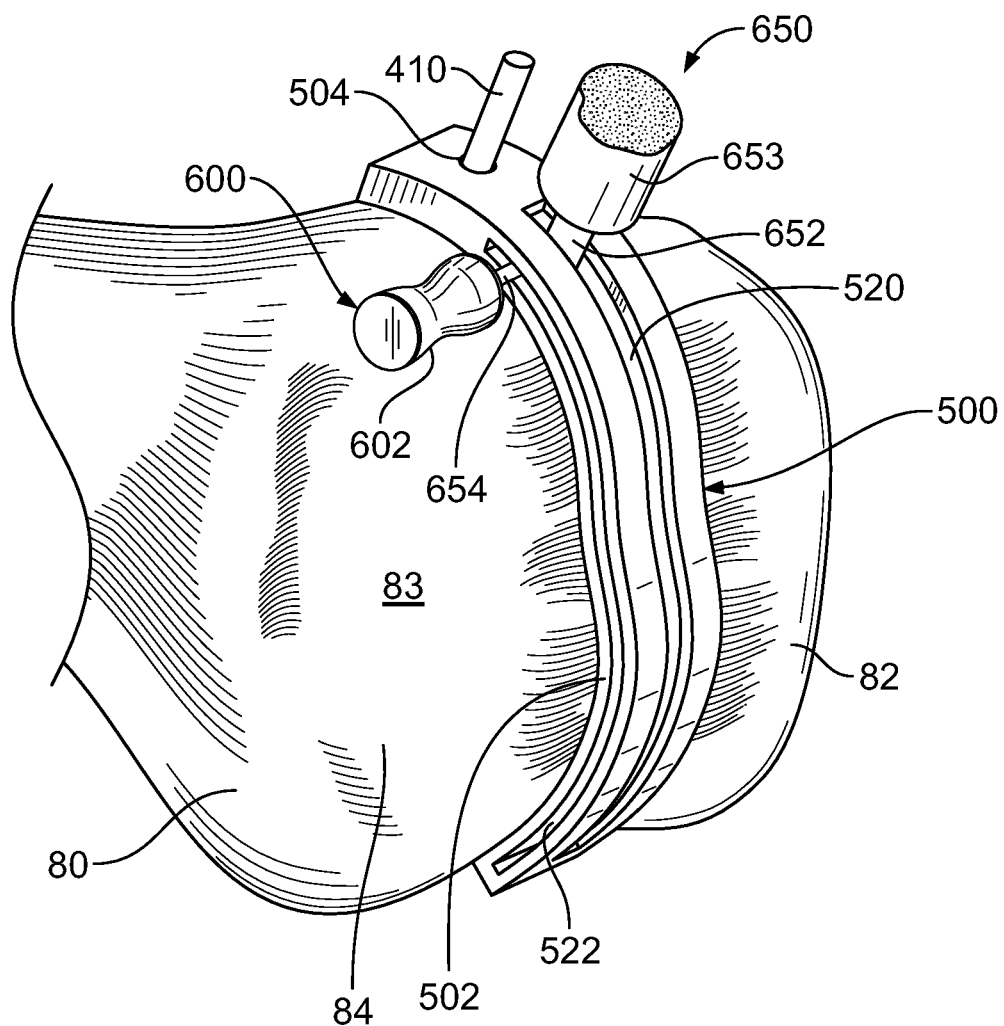
FIG. 9 is an environmental perspective view of the patient-specific guide of FIG. 7 shown with the resurfacing tool of FIG. 8 according to the present teachings.

Referring to FIGS. 7-9, another bone surface preparation procedure and associated instruments according to the present teachings are illustrated. In this embodiment, the patient-specific alignment guide 300 of FIG. 4 or a similar patient-specific alignment guide is registered on the outer bone surface 83 of the bone 80 and used to guide and insert a reference pin 410 into the bone 80. The patent-specific alignment guide 300 is then removed, and the reference pin 410 is used to guide and position a patient-specific resurfacing guide 500 on the outer bone surface 83, as shown in FIG. 7. The patient-specific resurfacing guide 500 can guide a resurfacing or cutting tool 650 to remove cartilage and/or bone from the outer bone surface 83 in preparation for an implant, as shown in FIGS. 8 and 9 and discussed below.

More specifically and with continued reference to FIGS. 7-9, the patient-specific resurfacing guide 500 has a hole or other opening 504 for receiving the reference pin 410 and a patient-specific surface 502. The patient-specific surface 502 can be preoperatively configured to mirror (as a negative or inverse or complementary surface) and mate with a corresponding portion of the outer bone surface 83 of the bone 80. The reference pin 410 facilitates the registration of the patient-specific resurfacing guide 500, such that the patient-specific resurfacing guide 500 can have a small width relative to the width of the portion of the outer bone surface 83 to be resurfaced. Resurfacing can be effected on each side of the patient-specific resurfacing guide 500 simultaneously or sequentially. For example, when the bone 80 is a distal femur, the patient-specific resurfacing guide 500 can have a narrow width in the mediolateral direction and track a narrow area between the first and second (medial or lateral) femoral condyles 82, 84, such that first and second femoral condyles 82, 84 can be exposed for either simultaneous or sequential resurfacing, as discussed below.

The patient-specific resurfacing guide 500 can include an external elongated slot 520 along the sagittal plane of the bone 80. The elongated slot 520 defines a pair of side openings 522 (one of the pair is hidden from view in FIG. 9). The elongated slot 520 can guide the resurfacing tool 650 to resurface the outer bone surface 83. The resurfacing tool 650 can include a resurfacing member 600 and can be movably coupled and guided by the elongated slot 520 such that the resurfacing member 600 can remove articular cartilage from the bone 80 or otherwise prepare the outer bone surface 83 for receiving an implant. The resurfacing tool 650 can include a handle 653 and a shaft 652 coupled to the handle 653. The shaft 652 can be received in the slot 520 and move in the sagittal plane of the bone 80 (perpendicularly to the bone 80) along the slot 520. The resurfacing member 600 can be coupled to a rod or peg 654 that can pass through the side opening 522. The peg 654 can be removably coupled to the shaft 652 and oriented perpendicularly to the shaft 652. The resurfacing member 600 can have a resurfacing (cutting or abrading) surface 602 that matches and engages the outer bone surface 83. The resurfacing surface 602 can be patient-specific and configured during the preoperative plan of the patient to conform in mirror-image fashion with the outer bone surface 83 (with or without cartilage, depending on the procedure), as reconstructed in three-dimensional digital image from medical scans of the bone 80 of the patient.

The resurfacing member 600 can be coupled to the resurfacing tool 650 on one side of the patient-specific resurfacing guide 500 for resurfacing a corresponding side of the outer bone surface 83, such as the femoral condyle 84 in the illustration of FIG. 9. The resurfacing member 600 can then be removed and another resurfacing member 600 preoperatively configured to be patient-specific to the outer bone surface 83 of the opposite side of the patient-specific resurfacing guide 500 (femoral condyle 82) can be coupled to resurfacing tool 650 for completing the resurfacing of the outer bone surface 83. In some embodiments, a pair of resurfacing members 600, one on each side of the patient-specific resurfacing guide 500, can be coupled simultaneously, rather than sequentially, to the resurfacing tool 650.

Figure 10:
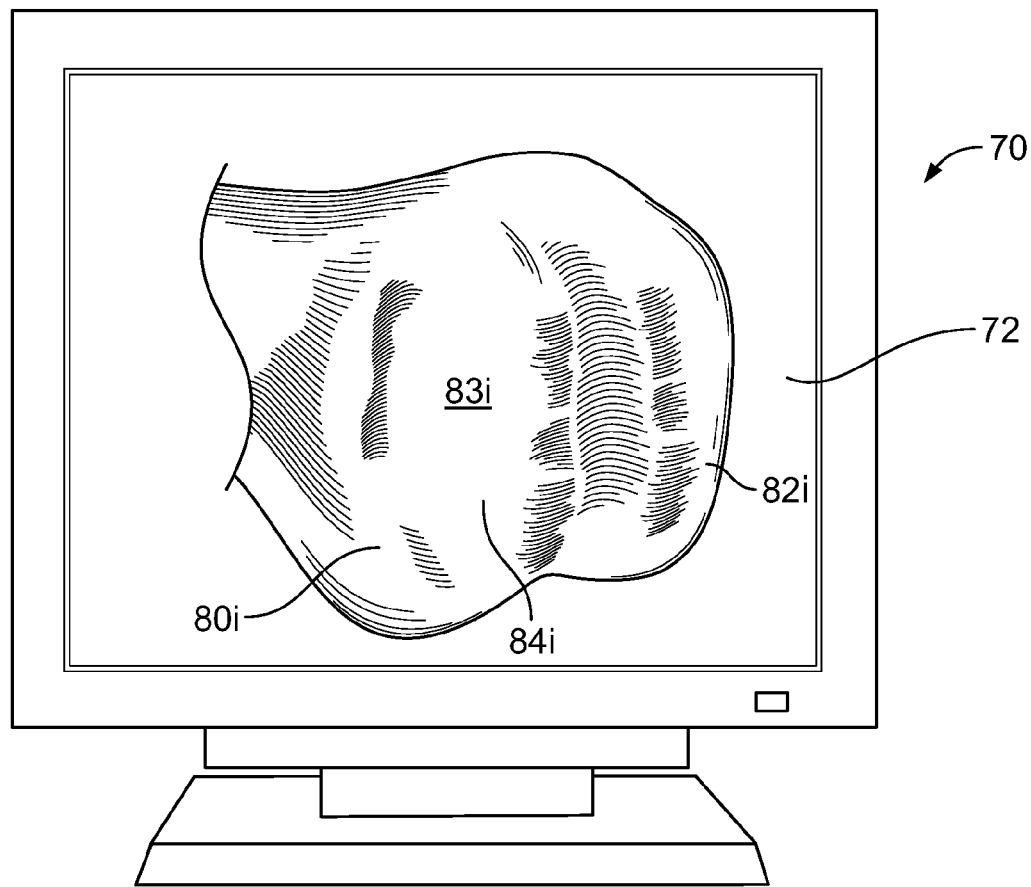
FIG. 10 is a front view of a digital display of an electronic device showing a three-dimensional digital image of a bone according to the present teachings.

Referring to FIGS. 10-13, a method for creating preoperatively a reconfigurable resurfacing or cutting instrument 800 is illustrated. The reconfigurable resurfacing instrument 800 can be reconfigured or "set" for each patient to take a patient-specific resurfacing shape. A three-dimensional digital image 80i of the patient's bone 80 can be reconstructed from medical scans of the patient using commercially available imaging software, as discussed above. The digital image 80i can be displayed on an electronic display 72 of a computer, computer terminal, portable or handheld tablet, mobile, cellular or other electronic device 70 equipped with a processor or communicating with a processor that runs the imaging software, as shown in FIG. 10. The digital image 80i can have a digital outer surface 83i corresponding to the outer bone surface 83, including, in the exemplary illustration of FIG. 10, digital femoral condyle images 82i, 84i.

Figure 11:
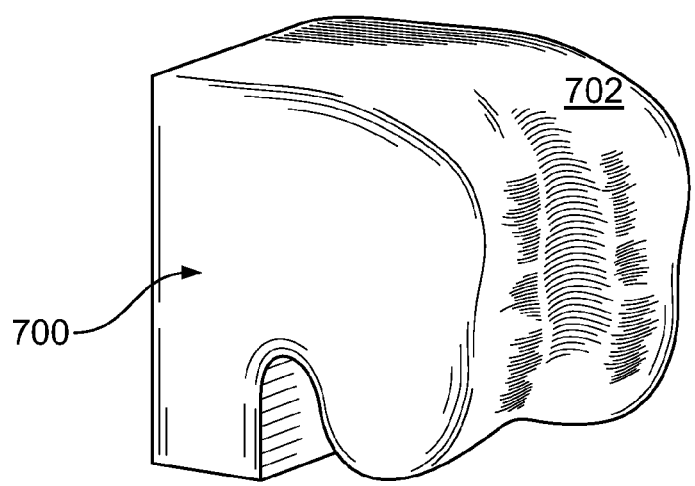
FIG. 11 is a perspective view of a physical bone model of a portion of the bone shown in FIG. 10 according to the present teachings.
Figure 12:
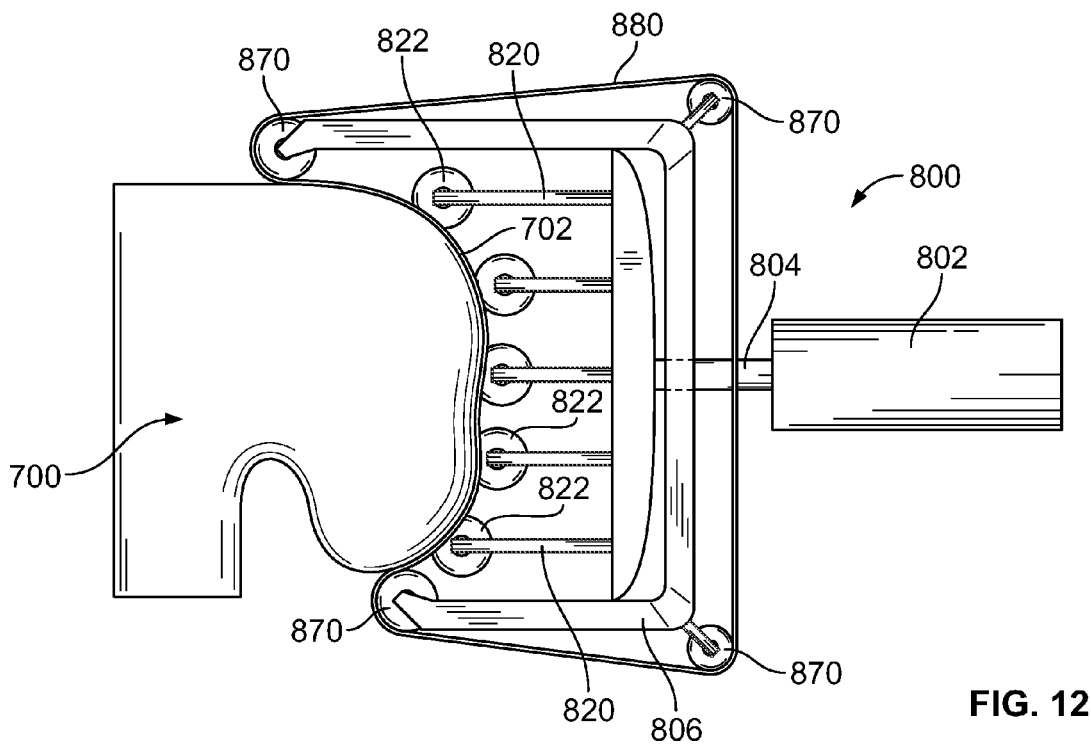
FIG. 12 is a side view of a reconfigurable resurfacing instrument shown with the bone model of FIG. 11 according to the present teachings.
Figure 13:
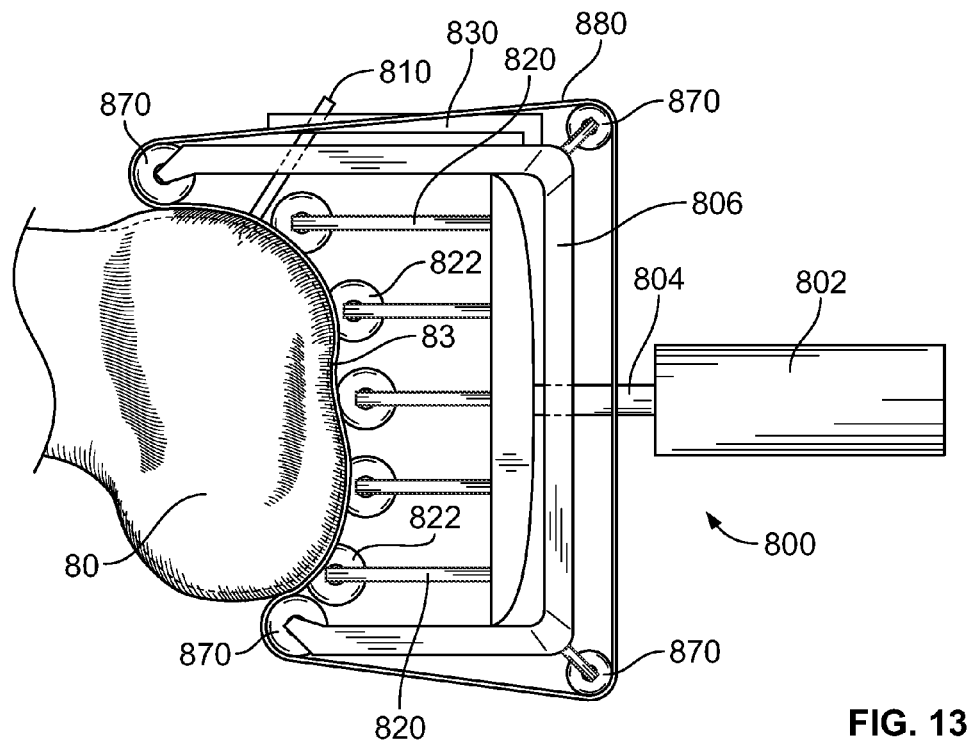
FIG. 13 is an environmental view of the reconfigured resurfacing instrument of FIG. 12 shown with the bone imaged in FIG. 10 according to the present teachings.

Referring to FIGS. 11-13, a patient-specific physical (not electronic) bone replica or model 700 can be created preoperatively from the digital image 80i using, for example, rapid prototyping, stereolithography or other manufacturing methods. The physical bone model 700 can have an outer surface 702 that replicates (is a copy of) the outer bone surface 83 (same as the digital outer surface 83i). The physical bone model 700 can be used as a setting surface to create and set an inverse shape on a movable and deformable resurfacing belt 880 of the reconfigurable resurfacing instrument 800 for removing cartilage from or otherwise abrading the outer bone surface 83 of the bone 80, as shown in FIG. 13.

The reconfigurable resurfacing instrument 800 can include a handle 802 and a frame 806 supporting the resurfacing belt 880 around pulleys 870 extending from the frame 806. A shaft 804 can couple the handle 802 to the frame 806. A plurality of rollers 822 can be connected to the frame 806 with adjustable, retractable, telescopic or spring-biased elongated elements 820, such as rods or bars. The adjustable elongated elements 820 can be spring-loaded against the resurfacing belt 880, such that when the resurfacing belt 880 is pushed against the outer surface 702 of the physical bone model 700, the lengths of the adjustable elongated elements 820 can change to allow the resurfacing belt 880 to deform and take the shape of a negative surface of the outer surface 702. The adjustable elongated elements 820 can then be locked at this configuration that sets the resurfacing belt 880 to a shape negative to the shape of the outer surface 702 of the physical bone model 700 that corresponds to the patient's bone 80, as discussed above. The reconfigurable resurfacing instrument 800 can be preoperatively reconfigured for a different patient using a new physical bone model 700 that is specific to the new patient. The resurfacing belt 880 is removable and can also be sterilizable and reusable, or can be a single-use disposable resurfacing belt 880.

In some embodiments, the resurfacing belt 880 can have a width (the dimension perpendicular to the side view of FIG. 12, or mediolateral dimension) sufficient to cover the entire outer surface 702 in FIG. 11, with the corresponding rollers 822 and elongated elements 820 arranged in a three-dimensional array. In other embodiments, the resurfacing belt 880 can have a width covering only a strip of the outer surface 702, with the corresponding rollers 822 and elongated elements 820 arranged in a two-dimensional array. In yet other embodiments, the width of the resurfacing belt 880 can be sufficient to resurface one of the femoral condyles (shown as 82i, 84i in the digital bone image 80i of FIG. 10). A narrow width of the resurfacing belt 880 can be selected for stability and ease of use. In such cases, the resurfacing belt 880 can also be reconfigured intraoperatively, as needed or at the surgeon's discretion, using the patient-specific bone model 700 for resurfacing other remaining portions of the outer bone surface 83. The physical bone model 700 can be included in the surgical kit for the specific patient, such that the reconfigurable resurfacing instrument 800 can be reconfigured intraoperatively to resurface additional portions of the outer bone surface 83 at the surgeon's discretion.

Referring to FIG. 13, in some embodiments the reconfigurable resurfacing instrument 800 can be additionally referenced to the bone 80 using a reference pin 810, which can be inserted into the bone 80 using a patient-specific alignment guide, such as the patient-specific alignment guide 300 shown with reference pin 410 and discussed above in connection with FIG. 4. The reconfigurable resurfacing instrument 800 can be registered to the reference pin 810 through a fixed or removable extension 830. Another reference pin 810 can also be placed in a patient-specific location and orientation in the physical bone model 700. For example, a pin-receiving bore for receiving the reference pin 810 can be incorporated in the physical bone model 700 in a preoperatively determined location and orientation. In some embodiments, instead of a resurfacing belt 880 other cutting elements can be used. For example, when the resurfacing belt 880 is not used, the rollers 822 can be replaced by cutting wheels (also referenced 822) at the distal ends of the elongated elements 820, such that the cutting wheels 822 define a boundary surface (or envelope surface) that is negative to the outer bone surface 83. In this respect, a sufficient number of cutting wheels 822 is used to contact and resurface the outer bone surface 83.

As discussed above, the present teachings provide various patient-specific guides and other instruments for guiding a cutting device to remove a small layer of cartilage and/or bone or otherwise prepare the bone for a patient-specific resurfacing implant or for a non-custom replacement implant. It is contemplated that elements and components shown in one exemplary embodiment can also be used in another embodiment. Further, the methods and devices described herein can be used for a bone surface of any joint, including knee, hip, shoulder, etc. The various devices and methods of the present teachings can be used to resurface an articular bone surface by removing cartilage or cartilage and a layer of underlying bone in orthopedic resurfacing procedures. Alternatively, the bone surface can be cut to remove bone and any overlying cartilage in preparation for implantation of a non-custom implant in orthopedic replacement procedures.

Example embodiments are provided so that this disclosure is thorough, and fully conveys the scope to those who are skilled in the art. Numerous specific details are set forth such as examples of specific components, devices, and methods, to provide a thorough understanding of embodiments of the present disclosure.

It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. Accordingly, individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for cutting or resurfacing an outer bone surface of a bone of a patient comprising:
mating a patient-specific surface of a patient-specific alignment guide on the outer bone surface of the bone, the patient-specific surface of the patient-specific alignment guide preoperatively configured as a negative surface of the outer bone surface;
inserting a reference pin into the bone through a guiding aperture of the patient-specific alignment guide;
removing the patient-specific alignment guide without removing the reference pin;
coupling a patient-specific resurfacing guide to the reference pin;
mating a patient-specific surface of the patient-specific resurfacing guide on the outer bone surface, the patient-specific surface of the patient-specific resurfacing guide preoperatively configured as a negative surface of the outer bone surface;
guiding a shaft of a resurfacing tool along an elongated slot of the patient-specific resurfacing guide on a sagittal plane of the bone;
coupling a patient-specific resurfacing member to the shaft of the resurfacing tool through a side slot of the patient-specific resurfacing guide, the side slot communicating with the elongated slot of the patient-specific resurfacing guide; and
resurfacing the outer bone surface using the patient-specific resurfacing member.

2. The method of claim 1, further comprising removing articular cartilage from the outer bone surface.

3. The method of claim 1, wherein coupling the resurfacing member to the shaft includes coupling the resurfacing member perpendicularly to the shaft.

4. The method of claim 1, further comprising removing articular cartilage from a femoral condyle.

5. The method of claim 1, further comprising mating the patient-specific resurfacing guide between medial and lateral femoral condyles such that the medial and lateral femoral condyles are exposed for either simultaneous or sequential resurfacing.

6. The method of claim 1, further comprising:
resurfacing a medial condyle of a distal femur using the patient-specific resurfacing member coupled to the resurfacing tool and guided by the patient-specific resurfacing guide; and
resurfacing a lateral condyle of the distal femur using the patient-specific resurfacing member coupled to the resurfacing tool and guided by the patient-specific resurfacing guide.

7. A method for cutting or resurfacing an outer bone surface of a bone of a patient comprising:
mating a patient-specific surface of a patient-specific alignment guide on the outer bone surface of the bone, the patient-specific surface of the patient-specific alignment guide preoperatively configured as a negative surface of the outer bone surface;
inserting a reference pin into the bone through a guiding aperture of the patient-specific alignment guide;
removing the patient-specific alignment guide without removing the reference pin;
coupling a patient-specific resurfacing guide to the reference pin;
mating a patient-specific surface of the patient-specific resurfacing guide on the outer bone surface, the patient-specific surface of the patient-specific resurfacing guide preoperatively configured as a negative surface of the outer bone surface;
guiding a resurfacing tool having a resurfacing member along an elongated slot in the patient-specific resurfacing guide;

guiding a shaft of the resurfacing tool along the elongated slot of the patient-specific resurfacing guide to guide the resurfacing member along a side slot communicating with the elongated slot during resurfacing; and resurfacing the outer bone surface using the resurfacing member coupled to the resurfacing tool.

8. The method of claim 7, further comprising resurfacing the outer bone surface using a patient-specific surface of the resurfacing member coupled to the resurfacing tool.

9. The method of claim 7, further comprising guiding the resurfacing tool along a sagittal plane of a distal femur.

10. The method of claim 7, wherein the side slot is positioned orthogonal to the elongated slot.

11. The method of claim 7, wherein resurfacing the outer bone surface includes resurfacing medial and lateral condyles of a distal femur either simultaneously or sequentially.

12. The method of claim 11, wherein mating the patient-specific surface of the patient-specific resurfacing guide includes mating the patient-specific surface of the patient-specific resurfacing guide between the medial and lateral condyles.

13. A method for cutting or resurfacing an outer bone surface of a bone of a patient, comprising:

mating a patient-specific surface of a patient-specific resurfacing guide on the outer bone surface, the patient-specific surface of the patient-specific resurfacing guide preoperatively configured as a negative surface of the outer bone surface;

guiding a shaft of a resurfacing tool along an elongated slot of the patient-specific resurfacing guide that extends along a sagittal plane of the bone;

coupling a patient-specific resurfacing member to the shaft through a side slot of the patient-specific resurfacing guide, the side slot communicating with the elongated slot of the patient-specific resurfacing guide; and resurfacing the outer bone surface using the patient-specific resurfacing member coupled to the resurfacing tool.

14. The method of claim 13, wherein the resurfacing member is coupled perpendicularly to the shaft of the resurfacing tool.

15. The method of claim 13, further comprising resurfacing a condyle of a distal femur with the resurfacing member.

16. The method of claim 15, further comprising:

mating a patient-specific surface of a patient-specific alignment guide on the outer bone surface of the bone, the first patient-specific surface of the patient-specific alignment guide preoperatively configured as a negative surface of the outer bone surface;

inserting a reference pin into the bone through a guiding aperture of the patient-specific alignment guide;

removing the patient-specific alignment guide without removing the reference pin; and coupling the patient-specific resurfacing guide to the reference pin.

17. The method of claim 13, further comprising mating the patient-specific resurfacing guide between medial and lateral femoral condyles such that the medial and lateral femoral condyles are exposed for either simultaneous or sequential resurfacing.

* * * * *

UNITED STATES PATENT AND TRADEMARK OFFICE
CERTIFICATE OF CORRECTION

PATENT NO.       : 8,764,760 B2
APPLICATION NO.  : 13/175142
DATED            : July 1, 2014
INVENTOR(S)      : Robert Metzger et al.

It is certified that error appears in the above-identified patent and that said Letters Patent is hereby corrected as shown below:

In the Specification

Column 5, Line 53; Delete "1008" and insert --100B--.

Column 5, Line 58; Delete "1008" and insert --100B--.

Column 6, Line 7; Delete "1008" and insert --100B--.

Column 6, Line 12; Delete "1048" and insert --104B--.

Column 6, Line 13; Delete "1008." and insert --100B.--.

Column 6, Line 14; Delete "1008" and insert --100B--.

Column 6, Line 55; Delete "1008." and insert --100B.--.

Column 9, Line 1; Delete "650" and insert --200--.

Signed and Sealed this
Eighteenth Day of November, 2014

Michelle K. Lee
*Deputy Director of the United States Patent and Trademark Office*